(12) United States Patent
Fontayne

(10) Patent No.: US 8,883,450 B2
(45) Date of Patent: Nov. 11, 2014

(54) SIGNAL PEPTIDE, AND USE THEREOF FOR PRODUCING RECOMBINANT PROTEINS

(75) Inventor: Alexandre Fontayne, La Madeleine (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 129 days.

(21) Appl. No.: 13/583,337

(22) PCT Filed: Mar. 17, 2011

(86) PCT No.: PCT/FR2011/050544
§ 371 (c)(1),
(2), (4) Date: Dec. 3, 2012

(87) PCT Pub. No.: WO2011/114063
PCT Pub. Date: Sep. 22, 2011

(65) Prior Publication Data
US 2013/0122546 A1 May 16, 2013

(30) Foreign Application Priority Data
Mar. 17, 2010 (FR) .................................... 10 51905

(51) Int. Cl.
| | | |
|---|---|---|
| *C12P 21/04* | (2006.01) | |
| *C12N 15/00* | (2006.01) | |
| *A61K 38/00* | (2006.01) | |
| *C07H 21/02* | (2006.01) | |
| *C12N 15/62* | (2006.01) | |
| *C07K 7/08* | (2006.01) | |

(52) U.S. Cl.
CPC ............... *C07K 7/08* (2013.01); *C07K 2319/02* (2013.01); *C12N 15/62* (2013.01)
USPC ..... 435/69.8; 435/69.1; 435/69.4; 435/69.52; 435/69.7; 435/68.1; 435/70.1; 435/70.3; 435/71.1; 435/320.1; 536/23.1; 530/326

(58) Field of Classification Search
None
See application file for complete search history.

(56) References Cited

U.S. PATENT DOCUMENTS

| | | | |
|---|---|---|---|
| 5,409,815 | A | 4/1995 | Nakagawa et al. |
| 7,008,623 | B1 | 3/2006 | Bonnefoy et al. |
| 2004/0229301 | A1 | 11/2004 | Wang |

FOREIGN PATENT DOCUMENTS

| | | |
|---|---|---|
| EP | 0 329 127 A2 | 8/1989 |
| EP | 0 356 335 A1 | 2/1990 |

OTHER PUBLICATIONS

International Search Report, dated Nov. 18, 2011, from corresponding PCT application.

*Primary Examiner* — Suzanne M Noakes
*Assistant Examiner* — Jae W Lee
(74) *Attorney, Agent, or Firm* — Young & Thompson

(57) ABSTRACT

A use of a signal peptide for producing a recombinant polypeptide of interest in an expression system, the signal peptide includes at least 12 amino acids of formula (I):

Figure 1:
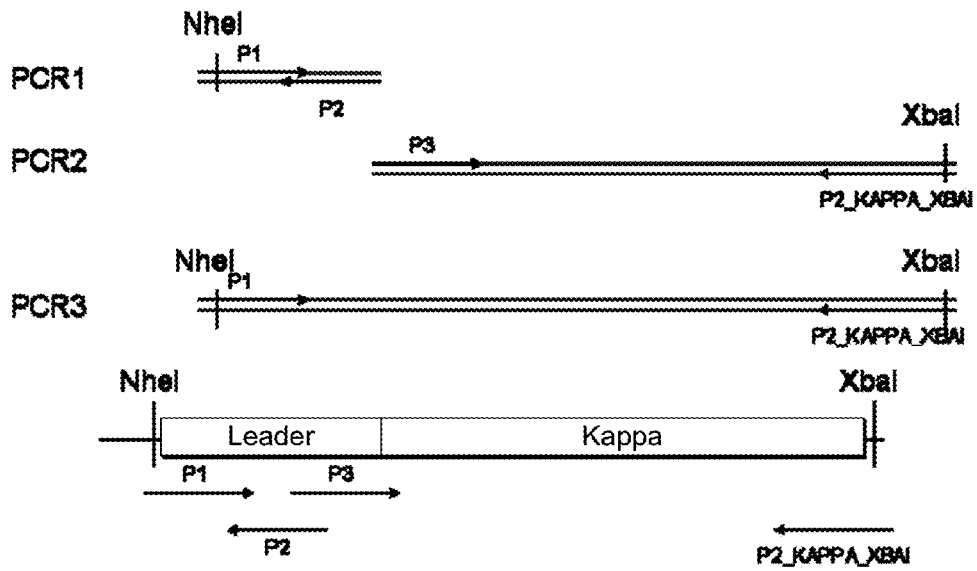

$(X1)_i X2 X3 X4 S X5 X6 X7$, wherein:
  X1 is a peptide containing from 3 to 6 amino acids, i equal to 0 or 1,
  X2 is a peptide containing from 3 to 9 hydrophobic amino acids,
  X3 is a peptide containing from 3 to 5 amino acids, the peptide including at least 3 contiguous or non-contiguous leucines
  X4 is a peptide containing from 2 to 5 amino acids chosen from Ala, Thr, Ser, Gln, Ile, Met,
  X5 is Ala or Val,
  X6 is Gln, Asn or His,
  X7 is Ala or Cys,
provided that when the signal peptide originates from a natural precursor of a specific protein, the polypeptide of interest is different from the protein.

26 Claims, 6 Drawing Sheets

SIGNAL PEPTIDE, AND USE THEREOF FOR PRODUCING RECOMBINANT PROTEINS

The present invention relates to a signal peptide, and use thereof for the production of recombinant proteins in eukaryotic expression systems.

A signal peptide (SP) is a segment of 12 to 30 amino acids situated at the N-terminal end of a protein serving to direct the latter to a particular cell compartment (organelle) or allowing it to be directed to the extracellular medium.

The signal peptide causes the protein to pass into the rough endoplasmic reticulum (RER) where it will be matured. Thus during the synthesis of the protein, a "signal recognition particle" (SRP) binds to both the signal peptide (receptor-ligand bond) and to the ribosome from which the signal peptide emerges. The SRP/ribosome complex is then recruited to the surface of the endoplasmic reticulum by a membrane receptor, the SRP receptor, itself bound to the translocation channel (PCC). During this event the synthesis of the protein is suspended as the SRP blocks the access of the elongation factors, eEF-1 and eEF-2. This recruitment is followed by hydrolysis of the GTP to GDP and Pi, releasing the SRP particle.

The nascent protein, as it grows, follows the channel to pass completely into the lumen of the reticulum. The hydrophobic nature of the signal peptide (α-helix) also allows interaction with the phospholipids of the membrane.

During their synthesis, the proteins intended for secretion retain their signal peptide which persists in the α-helix form as the site of insertion into the membrane, allowing chaperone proteins such as BIP to bind to the polypeptide chain being synthesized in order to ensure its folding. The post-translational modifications such as glycosylation start in the ER and are completed in the Golgi, where the glycans are matured.

The N-terminal end of a signal peptide is divided into 3 regions, namely the n-region, the h-region and the c-region, each with a different length and properties. The n-region is situated at the N-terminal end of the signal peptide, whereas the c-region is at the C-terminal end of the signal peptide. The h-region is situated between the n-region and the c-region. The n- and h-regions constitute the core of the signal peptide on which the directing is dependent whereas the peptidase cleavage is dependent on the c-region. It is known that the n-region contains little arginine, whilst the h-region is a hydrophobic region. It is also known that the residues in the c-region tend to be small non-polar residues.

During the expression of a recombinant protein in a eukaryotic system, the presence or absence of signal peptide, or choice of the latter can directly influence the productivity of said recombinant protein, in other words the quantity of protein secreted by the cells containing a transgene reported per unit volume.

For example, certain heterologous proteins are toxic to the survival or growth of the host cells, certain others are not toxic, but inhibit the growth of the host cells. In these cases, the secretion of such a toxic protein towards the extracellular medium, makes it possible to avoid the toxicity or growth inhibition linked to the expression of the heterouous recombinant protein.

From an industrial production point of view, a recombinant protein capable of being secreted in an extracellular medium is much more advantageous than a recombinant protein accumulated in the host cell, as the process of purification of a secreted protein is generally simpler than that of a protein which has accumulated in a cell. Furthermore, this makes it possible to dispense with the co-purification of immature proteins which can interfere with or reduce the activity of the protein of interest.

Moreover, given that not all the signal peptides have the same secretory power, the endogenous signal peptide of a protein capable of being secreted is not always sufficiently effective for the industrial production of the protein in question.

Certain signal peptides have already been designed for the expression of recombinant proteins in certain expression systems. The patent EP 0 329 127 describes a signal peptide intended for the expression of recombinant proteins in yeast cells. The patent EP 0 356 335 described a bacterial signal peptide for improving the periplasmic production of heterologous polypeptides in bacteria.

However, these signal peptides do not make it possible to optimize the expression of recombinant proteins in the higher eukaryotic cell lines including mammal cells, an expression system often essential to the production of numerous therapeutic recombinant proteins, such as antibodies.

As a result, it follows that there is a great need to make available a universal signal peptide, making it possible to improve the expression and secretion of recombinant proteins in a higher eukaryotic cell line.

The present invention is based on an unexpected finding made by the Inventors during a study of the secretion ability, on the one hand, of a light chain of an antibody bound to the different signal peptides designed by the Inventors and, on the other hand, of a whole IgG. In fact, certain signal peptides make it possible to significantly increase the secretion of an immunoglobulin light chain or a whole immunoglobulin.

A subject of the present invention is the use of a signal peptide for the production and secretion of a recombinant polypeptide of interest in an expression system, the quantity of the polypeptide secreted using said signal peptide being at least equal to the quantity of said polypeptide secreted using its natural signal peptide, the biological activity of the polypeptide of interest being retained compared with that of the polypeptide of interest produced by its natural signal peptide, said signal peptide comprising at least 12 amino acids of formula (I):

$$(X1)_iX2X3X4SX5X6X7,$$

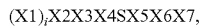

in which: (includes the three peptides)

X1 is a peptide containing from 3 to 6 amino acids, i equal to 0 or 1,

X2 is a peptide containing from 3 to 9 hydrophobic amino acids,

X3 is a peptide containing from 3 to 5 amino acids, said peptide comprising at least 3 contiguous or non-contiguous leucines, X4 is a peptide containing from 2 to 5 amino acids chosen from Ala, Thr, Ser, Gln, Ile, Met, X5 is Ala or Val, X6 is Gln, Asn or His, X7 is Ala or Cys, provided that:

when said signal peptide originates from a natural precursor of a specific protein, said polypeptide of interest is different from said protein, and when the signal peptide is MAWVWTLLFL-MAAAQSAQA, said polypeptide of interest is not an anti-CD23 antibody, irrespective of the polypeptide of interest which can be bound to one of said signal peptides in order to be secreted in an extracellular medium.

By "signal peptide", is meant a peptide chain of approximately 10 to 30 amino acids, situated within a polypeptide chain, serving to direct the latter to a particular cell compartment (organelle) or allowing it to be directed to the extracellular medium.

Said signal peptide according to the invention is preferably situated at the N-terminal end of the polypeptide of interest.

The use of a signal peptide makes it possible to increase the secretion rate of a polypeptide of interest. It should be noted that the signal peptide used in the invention is different from the signal peptide naturally associated with a specific protein.

By "recombinant polypeptide of interest" is meant a polypeptide produced in vitro by the transcriptional and translational machinery of a cell in culture, or more generally produced by living cells (in vitro or in vivo) having received an exogenous DNA encoding for said polypeptide.

Said signal peptide makes it possible to produce a recombinant polypeptide of interest secreted in a quantity at least equal to the quantity of said polypeptide secreted using its natural signal peptide.

Furthermore, such a polypeptide of interest produced using a signal peptide according to the invention retains the biological activity of the polypeptide of interest produced by its natural signal peptide.

A signal peptide according to the invention can make it possible to produce a recombinant polypeptide of interest in an expression system in vitro, for example in a cell culture.

A signal peptide according to the invention can also make it possible to produce a recombinant polypeptide of interest in an expression system in vivo, for example in transgenic animals, such as goats, sheep, bison, camels, cows, pigs, rabbits, horses, rats, mice or llamas.

A signal peptide according to the invention can be used either in the production of a protein possessing a natural signal peptide, or in the production of a protein which possesses no natural signal peptide, such as a fusion protein or an artificial protein.

In a particular embodiment, the invention relates to the use of a signal peptide as defined above, in which said signal peptide is represented by the formula (II):

$$M(X1)_i X2 X3 X4 S X5 X6 X7,$$

in which X1, i, X2, X3 X4, X5X6 and X7 have the meanings indicated in formula I.

In an embodiment of the use of a signal peptide as defined above, the peptide X3 comprises at least 3 contiguous leucines.

By "3 contiguous leucines", is meant three leucines bound successively and directly one after the other, no other amino acid being inserted among these three leucines.

In another embodiment of the use of a signal peptide as defined above, the peptide X3 comprises at least 3 non-contiguous leucines.

By "3 non-contiguous leucines", is meant that at least one of the three leucines is not bound directly to one of the other two leucines and that at least one amino acid different from leucine is inserted between at least two of the three leucines.

By way of example, three non-contiguous leucines can comprise 2 leucines bound to each other directly and successively, a third leucine being bound to these two leucines via at least one amino acid different from leucine.

By way of example, three non-contiguous leucines can also be separated from each other by at least one amino acid different from leucine. In other words, these three leucines are bound to each other by at least one amino acid different from leucine situated between each of the leucines.

In a particular embodiment, the invention relates to the use of a signal peptide as defined above, in which:
X1, X2 and X4 have the meanings indicated in formula I,
i=1,
X3 is a peptide constituted by leucines, represented by Ln, in which n is the number of leucines, n being a number greater than or equal to 3,
X4 is a peptide containing from 2 to 5 amino acids chosen from Ala, Thr, Ser, Gln, Ile,
X5 is Ala,
X6 is Gln or Asn,
X7 is Ala,
said peptide comprising the following sequence of amino acids: X1X2LnX4SAX6A.

In a more particular embodiment, the invention relates to the use of a signal peptide represented by the sequence of amino acids SEQ ID NO: 1 (MRWSWIFLLLLSITSANA).

In another particular embodiment, the invention relates to the use of a signal peptide as defined above, in which:
X1 and X2 have the meanings indicated in formula I,
i=1,
X3 is a peptide comprising 3 non-contiguous leucines, of which 2 leucines are separated by another hydrophobic amino acid chosen from Gly, Ala, Val, Ile, Pro, Phe, Trp,
X4 is a peptide containing from 2 to 5 amino acids chosen from Ala, Thr, Ser, Gln, Ile,
X5 is Val,
X6 is His,
X7 is Cys,
said peptide comprising the following sequence of amino acids: X1X2X3X4SVHC.

In a more particular embodiment, the invention relates to the use of a signal peptide represented by the sequence of amino acids SEQ ID NO: 2 (MRWSWIFLFLLSITASVHC), provided that this signal peptide is not utilized in the production of the heavy chain of an anti-AMHRII antibody. The signal peptide represented by the sequence SEQ ID NO: 2 is encoded by the nucleic acid represented by the sequence SEQ ID NO: 28 (atgcgatggagctggatctttctcttc-ctcctgtcaataactgcaagtgtccattgc).

In another particular embodiment, the invention relates to the use of a signal peptide as defined above, in which:
X1, X2 and X4 have the meanings identical to formula I,
i=0,
X3 is a peptide comprising 3 non-contiguous leucines, of which 2 leucines are separated by another hydrophobic amino acid chosen from Gly, Ala, Val, Ile, Pro, Phe, Trp,
X5 is Ala,
X6 is Gln,
X7 is Ala,
said peptide comprising the following sequence of amino acids: X2X3X4SAQA.

In a more particular embodiment, the invention relates to the use of a signal peptide represented by the sequence of amino acids SEQ ID NO: 3 (MAWVWTLLFL-MAAAQSAQA), provided that this signal peptide is not utilized in the production of the heavy chain of an anti-CD5 antibody, or of an anti-CD23 antibody. The signal peptide represented by the sequence SEQ ID NO: 3 is encoded by the nucleic acid represented by the sequence SEQ ID NO: 29 (atggcttgggtgtggaccttgctattc-ctgatggcagctgcccaaagtgcccaagca).

The in vitro expression system can be any expression system known to a person skilled in the art, for example the expression of heterologous proteins in bacteria, yeasts, insect cells or other eukaryotic cell lines.

Advantageously, the use of a signal peptide according to the invention is implemented in a higher eukaryotic cell line.

More advantageously, the abovementioned higher eukaryotic cell line can be chosen from SP2/0, (SP2/0-Ag 14), NS0, other rat myelomas such as IR983F, human lines such as Namalwa, Wil-2, Jurkat, Molt-4, PER.C6, HEK293T/17, HEK293, HEK-293.2, Vero, Cos-1 or Cos-7, BHK, CHO-K-1, CHO-Lec1, CHO-Lec10, CHO-Lec13, CHO Pro-5, CHO DX B11 and CHO DG44 and other lines such as EBx with in particular EB66K6H6, and P3X63Ag8.653 and YB2/0, CHO-S and HEK-293F.

Such a recombinant polypeptide of interest produced using a signal peptide according to the invention can be any protein of interest, or form part of a protein of interest. Such a polypeptide of interest can be chosen from, by way of example, a hormone, an immunoglobulin enzyme, a whole immunoglobulin or any fragment derived from an immunoglobulin, a protein involved in the immune response such as cytokines, interleukins, complement factors, a chimeric protein, or other therapeutic protein such as coagulation factors, extracellular matrix proteins, or soluble receptors.

In an advantageous embodiment, a signal peptide according to the invention makes it possible to produce in the extracellular medium, a recombinant polypeptide of interest, in which the primary and secondary structures of said polypeptide are identical to those of the polypeptide produced using its natural signal peptide.

In a particular embodiment of the invention, the signal peptide MRWSWIFLLLLSITSANA according to the invention makes it possible to produce in the extracellular medium, a recombinant polypeptide of interest in which the primary and secondary structures of said polypeptide are identical to those of the polypeptide produced using its natural signal peptide.

A subject of the present invention is also a signal peptide comprising a sequence of at least 12 amino acids of formula III:

X1X2X3X4SX5X6X7, in which:
X1 is a peptide containing from 3 to 6 amino acids,
X2 is a peptide containing from 3 to 9 hydrophobic amino acids,
X3 is a peptide containing from 3 to 5 amino acids, said peptide comprising at least 3 contiguous leucines,
X4 is a peptide containing from 2 to 5 amino acids chosen from Ala, Thr, Ser, Gln, Ile,
X5 is Ala,
X6 is Gln or Asn,
X7 is Ala.

The leucines situated in the h-region of the abovementioned signal peptides make it possible to create a stretch of leucine.

In the signal peptides described above, the region "SAX6A" corresponds to the peptidase recognition site. The amino acid represented by X6 can be a glutamine or an asparagine, as they have similar physicochemical properties.

In an advantageous embodiment, the signal peptides according to the invention correspond to formula (IV): MX1X2X3X4SX5X6X7, in which X1, X2, X3 X4, X5 X6 and X7 have the meanings indicated in formula III.

In a particular embodiment, the invention relates to the signal peptides corresponding to formula III or to formula IV, in which:
X3 is a peptide containing 4 contiguous leucines,
the peptide X1 is RWS,
X2, X4 and X6 have the meanings indicated in formula III, the signal peptide corresponding to the following formula: RWSX2X3X4SAX6A.

In another particular embodiment, the invention relates to the signal peptides corresponding to formula III or to formula IV, in which:
X3 is a peptide containing 4 contiguous leucines,
the peptide X2 is WIF,
X1, X4 and X6 have the meanings indicated in formula III, the signal peptide corresponding to the following formula: X1WIFX3X4SAX6A.

In another particular embodiment, the invention relates to the signal peptides corresponding to formula III or to formula IV, in which:
X3 is a peptide containing 4 contiguous leucines,
the peptide X4 is SIT,
X1, X2 and X6 have the meanings indicated in formula III, the signal peptide corresponding to the following formula: X1X2X3SITSAX6A.

In a particularly advantageous embodiment, the signal peptide according to the invention comprises or consists of the sequence of amino acids: MRWSWIFLLLLSITSANA (SEQ ID NO: 1).

A subject of the invention is also the nucleic acids encoding one of the signal peptides corresponding to formula III or formula IV.

In a particular embodiment, the nucleic acid according to the invention encodes a signal peptide comprising at least 12 amino acids of formula III: X1X2X3X4SX5X6X7, in which:
X1 is a peptide containing from 3 to 6 amino acids,
X2 is a peptide containing from 3 to 9 hydrophobic amino acids,
X3 is a peptide containing from 3 to 5 amino acids, said peptide comprising at least 3 contiguous leucines
X4 is a peptide containing from 2 to 5 amino acids chosen from Ala, Thr, Ser, Gln, Ile,
X5 is Ala,
X6 is Gln or Asn,
X7 is Ala.

In a more particular embodiment, the nucleic acid according to the invention encodes a signal peptide of formula (IV): M X1X2X3X4SX5X6X7, in which X1, X2, X3 X4, X5 X6 and X7 have the meanings indicated in formula III.

In an even more particular embodiment, the nucleic acid according to the invention encodes a signal peptide corresponding to formula III or to formula IV, in which:
X3 is a peptide containing 4 contiguous leucines,
the peptide X1 is RWS.

In another even more particular embodiment, the nucleic acid according to the invention encodes a signal peptide corresponding to formula III or to formula IV, in which:
X3 is a peptide containing 4 contiguous leucines,
the peptide X2 is WIF.

In another even more particular embodiment, the nucleic acid according to the invention encodes a signal peptide corresponding to formula III or to formula IV, in which:
X3 is a peptide containing 4 contiguous leucines,
the peptide X4 is SIT.

The nucleotide sequences according to the invention can be deduced from the amino acid sequences of the signal peptides according to the invention. The respective genetic codons of each amino acid in the eukaryotes are known to a person skilled in the art.

In a particularly advantageous embodiment of the invention, the nucleic acid according to the invention encodes a peptide represented by the sequence SEQ ID NO: 1: MRWSWIFLLLLSITSANA.

More particularly, this nucleotide sequence is the following sequence (SEQ ID NO: 4): 5'-atgcgatggagctggatcttcctgctgctgctgagcatcaccagcgccaacgcc-3'.

The nucleic acids encoding one of the signal peptides according to the invention can be added to the 5' end of a nucleic acid encoding a polypeptide of interest by any method known to a person skilled in the art, for example, the PCR technique.

A subject of the present invention is also a precursor of a recombinant polypeptide of interest, in which the signal peptide comprises at least 12 amino acids of formula (I): $(X1)_i$X2X3X4SX5X6X7, in which:

X1 is a peptide containing from 3 to 6 amino acids, i equal to 0 or 1,

X2 is a peptide containing from 3 to 9 hydrophobic amino acids,

X3 is a peptide containing from 3 to 5 amino acids, said peptide comprising at least 3 contiguous or non-contiguous leucines X4 is a peptide containing from 2 to 5 amino acids chosen from Ala, Thr, Ser, Gln, Ile, Met, X5 is Ala or Val, X6 is Gln, Asn or His, X7 is Ala or Cys, provided that when said signal peptide originates from a natural precursor of a specific protein, said polypeptide of interest is different from said protein, and when the signal peptide is MAWVWTLLFLMAAAQSAQA, said polypeptide of interest is not an anti-CD23 antibody, irrespective of the polypeptide of interest which can be bound to one of said signal peptides in order to be secreted in the extracellular medium.

In a particular embodiment, a precursor according to the invention comprises a signal peptide corresponding to formula III or to formula IV described above, in which X1, X2, X3, X4, X5, X6 and X7 have the meanings indicated in formula III.

In a particular embodiment, a precursor according to the invention comprises a signal peptide comprising the following sequence of amino acids: X1X2LnX4SAX6A, in which:

X1 is a peptide containing from 3 to 6 amino acids,

X2 is a peptide containing from 3 to 9 hydrophobic amino acids, n is the number of leucines, n being a number greater than or equal to 3, X4 is a peptide containing from 2 to 5 amino acids chosen from Ala, Thr, Ser, Gln, Ile, X6 is Gln or Asn.

In a particularly advantageous embodiment, a precursor of a polypeptide of interest according to the invention comprises a signal peptide consisting of the following sequence of amino acids: MRWSWIFLLLLSITSANA (SEQ ID NO: 1).

In another particular embodiment, a precursor according to the invention comprises a signal peptide comprising the following sequence of amino acids: X1X2X3X4SVHC, in which:

X1 is a peptide containing from 3 to 6 amino acids,

X2 is a peptide containing from 3 to 9 hydrophobic amino acids,

X3 is a peptide comprising 3 non-contiguous leucines, of which 2 leucines are separated by another hydrophobic amino acid chosen from Gly, Ala, Val, Ile, Pro, Phe, Trp, X4 is a peptide containing from 2 to 5 amino acids chosen from Ala, Thr, Ser, Gln, provided that when said signal peptide originates from a natural precursor of a specific protein, said polypeptide of interest is different from said protein.

In a particularly advantageous embodiment, a precursor of a polypeptide of interest according to the invention comprises a signal peptide consisting of the following sequence of amino acids: MRWSWIFLFLLSITASVHC (SEQ ID NO: 2), provided that said polypeptide of interest is different from the gamma chain of an anti-AMHRII antibody.

In another particular embodiment, a precursor according to the invention comprises a signal peptide comprising the following sequence of amino acids: X2X3X4SAQA, in which:

X2 is a peptide containing from 3 to 9 hydrophobic amino acids,

X3 is a peptide comprising 3 non-contiguous leucines, of which 2 leucines are separated by another hydrophobic amino acid chosen from Gly, Ala, Val, Ile, Pro, Phe, Trp, Leu X4 is a peptide containing from 2 to 5 amino acids chosen from Ala, Thr, Ser, Gln, Met, provided that when said signal peptide originates from a natural precursor of a specific protein, said polypeptide of interest is different from said protein.

In a particularly advantageous embodiment, a precursor of a polypeptide of interest according to the invention comprises a signal peptide consisting of the following sequence of amino acids: MAWVWTLLFLMAAAQSAQA (SEQ ID NO: 3), provided that said polypeptide of interest is different from the gamma chain of an anti-CD5 antibody, and that said polypeptide of interest is different from an anti-CD23 antibody.

In a particular embodiment, such a precursor according to the invention is a precursor of a recombinant polypeptide of interest chosen from a hormone, an enzyme, an immunoglobulin chain, a whole immunoglobulin or any fragment derived from an immunoglobulin, a protein involved in the immune response such as cytokines, interleukins, complement factors, a chimeric protein, or other therapeutic proteins such as coagulation factors, extracellular matrix proteins or soluble receptors.

In a more particular embodiment, such a precursor according to the invention is a precursor of a recombinant polypeptide of interest chosen from a light chain of an antibody, and/or a heavy chain of an antibody.

A subject of the present invention is a nucleic acid encoding one of the precursors of a recombinant polypeptide of interest according to the present invention.

A subject of the present invention is an expression vector comprising a nucleic acid as described above, encoding a precursor of a recombinant polypeptide of interest as described above.

In a particular embodiment, the vector according to the invention also comprises the genetic means, in particular the replication origins, the promoters, making it possible to control the expression of the abovementioned recombinant polypeptide of interest.

Said expression vector according to the invention can be capable of expressing the abovementioned recombinant polypeptide of interest in a higher eukaryotic cell line after a transient or stable transfection, said line being able to be advantageously chosen from SP2/0, (SP2/0-Ag 14), NS0, other rat myelomas such as IR983F, human lines such as Namalwa, Wil-2, Jurkat, Molt-4, PER.C6, HEK293T/17, HEK293, HEK-293.2, Vero, Cos-1 or Cos-7, BHK, CHO-K-1, CHO-Lec1, CHO-Lec10, CHO-Lec13, CHO Pro-5, CHO DX B11 and CHO DG44 and other lines such as EBx with in particular EB66K6H6, and P3X63Ag8.653, YB2/0, CHO-S and HEK-293F.

The present invention also relates to a method for producing a recombinant polypeptide of interest, comprising:

the addition of a nucleic acid encoding a signal peptide comprising at least 12 amino acids of formula (I):

(X1)<sub>i</sub>X2X3X4SX5X6X7, in which:
X1 is a peptide containing from 3 to 6 amino acids, i equal to 0 or 1,
X2 is a peptide containing from 3 to 9 hydrophobic amino acids,
X3 is a peptide containing from 3 to 5 amino acids, said peptide comprising at least 3 contiguous or non-contiguous leucines
X4 is a peptide containing from 2 to 5 amino acids chosen from Ala, Thr, Ser, Gln, Ile, Met,
X5 is Ala or Val,
X6 is Gln, Asn or His,
X7 is Ala or Cys,
to the 5' end of a nucleic acid encoding a recombinant polypeptide of interest, in order to obtain a nucleic acid encoding the precursor of the abovementioned recombinant polypeptide of interest, provided that when said signal peptide originates from a natural precursor of a specific protein, said polypeptide of interest is different from said protein,
the cloning of the artificial nucleic acid obtained in the previous stage to an expression vector, in order to obtain a vector capable of expressing the precursor of the abovementioned recombinant polypeptide of interest, and
the transfection of a higher eukaryotic cell line by the expression vector comprising said artificial nucleotide sequence and the expression of said nucleotide sequence,
the recovery of the recombinant polypeptide of interest secreted in the culture medium.

The recovery of a recombinant polypeptide can be carried out by any method known to a person skilled in the art, for example precipitation, centrifugation, chromatography elution. This stage can be also associated with a stage of purification of the polypeptide.

An expression vector utilized in the abovementioned process according to the invention can be any expression vector known to a person skilled in the art, for example a vector making it possible to express in vitro a polypeptide in a higher eukaryotic cell line in transient or stable transfection.

In a particular embodiment of the production method according to the invention, the eukaryotic cell line is chosen from the cell lines: SP2/0, (SP2/0-Ag 14), NS0, other rat myelomas such as IR983F, human lines such as Namalwa, Wil-2, Jurkat, Molt-4, PER.C6, HEK293T/17, HEK293, HEK-293.2, Vero, Cos-1 or Cos-7, BHK, CHO-K-1, CHO-Lec1, CHO-Lec10, CHO-Lec13, CHO Pro-5, CHO DX B11 and CHO DG44 and other lines such as EBx with in particular EB66K6H6, and P3X63Ag8.653, YB2/0, CHO-S and HEK-293F.

In a particular embodiment of the production method according to the invention, the recombinant polypeptide of interest is chosen from a hormone, an enzyme, an immunoglobulin chain, a whole immunoglobulin or any fragment derived from an immunoglobulin, a protein involved in the immune response, such as cytokines, interleukins, complement factors, a chimeric protein, or any other therapeutic proteins, such as coagulation factors, extracellular matrix proteins, soluble receptors.

In a particular embodiment of the invention, the present invention relates to a method for producing recombinant antibodies:
the addition of a nucleic acid encoding the signal peptide MRWSWIFLLLLSITSANA to the 5' end of a nucleic acid encoding an immunoglobulin chain, in order to obtain a nucleic acid encoding the precursor of an immunoglobulin chain,
the cloning of the artificial nucleic acid obtained in the previous stage to an expression vector, in order to obtain a vector capable of expressing the precursor of an immunoglobulin chain,
the transfection of a higher eukaryotic cell line chosen from PER.C6, YB2/0, CHO-S and HEK 293, by the expression vector(s) comprising said artificial nucleotide sequence and the expression of said nucleotide sequence,
the recovery of the antibody secreted in the culture medium.

In a more particular embodiment of the invention and in the context of the production of an antibody, the signal peptide used for the production of the heavy chain is the same as that used for the production of the light chain.

In an even more particular embodiment of the invention for the production of an antibody, the signal peptide MRWSWIFLLLLSITSANA is used to produce both the heavy chain and the light chain of said antibody of interest.

The present invention is illustrated, by way of example only, by the figures and the examples below.

FIG. 1 represents the principle used for the addition of the signal peptides to the 5' end of the T125 kappa chain. The arrows indicate the different primers used for the assembly PCR.

Figure 2A:
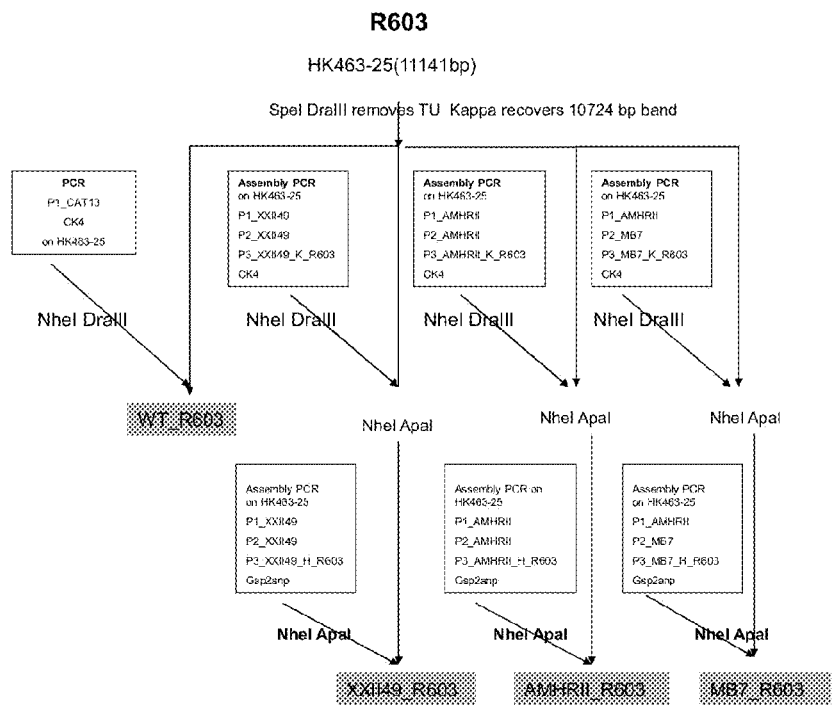

FIG. 2A represents the principle used for preparing the expression vectors encoding the antibody anti-CD20 (R603) and making it possible to evaluate the secretory power of the SPs on whole IgGs. The boxes represent the heavy or light chain variable parts to be cloned in the vector. The final vectors which form the subject of the evaluations are underlined in grey.

Figure 2B:
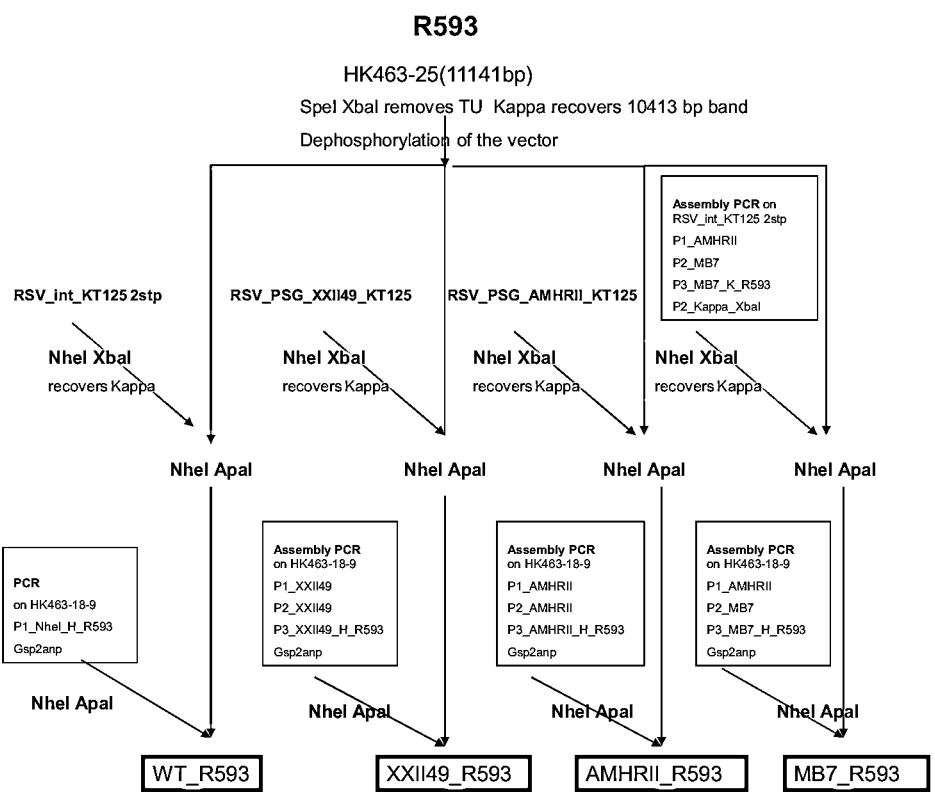

FIG. 2B represents the principle used for preparing the expression vectors encoding the anti-RhD (R593) antibody and making it possible to evaluate the secretory power of the SP on whole IgGs. The boxes represent the heavy or light chain variable parts to be cloned in the vector. The final vectors which form the subject of the evaluations are underlined in grey.

Figure 3:
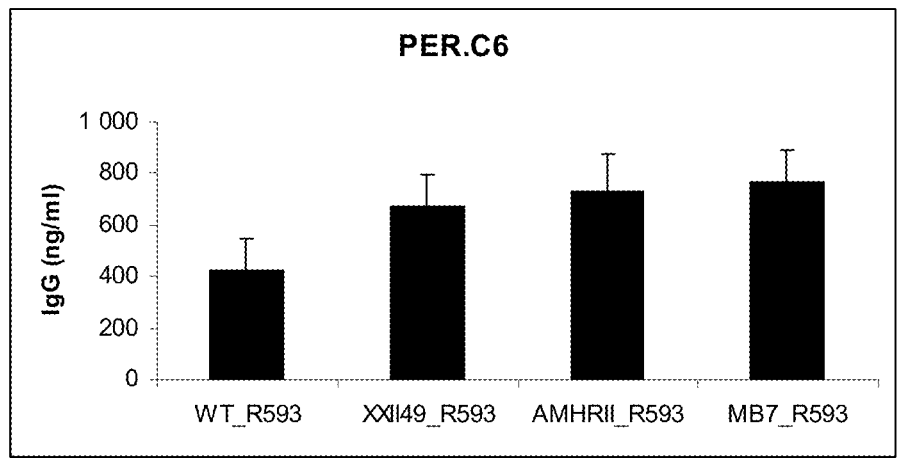

FIG. 3 shows a comparison of the effect of 3 signal peptides, including 12G4 (represented by the sequence SEQ ID NO: 2), XXII49 (represented by the sequence SEQ ID NO: 3) and MB7 (represented by the sequence SEQ ID NO: 1), on the secretion of a whole anti-RhD antibody (R593), in the PER.C6 cell line evaluated in transient transfection. The four columns, from left to right, represent respectively the secretion rate of the R593 antibody bound respectively to its initial signal peptides (heavy chain, light chain), to the signal peptide 12G4, to the signal peptide XXII49 and to the signal peptide according to the invention MB7. The y-axis represents the concentration of R593 antibody secreted in the culture medium.

Figure 4:
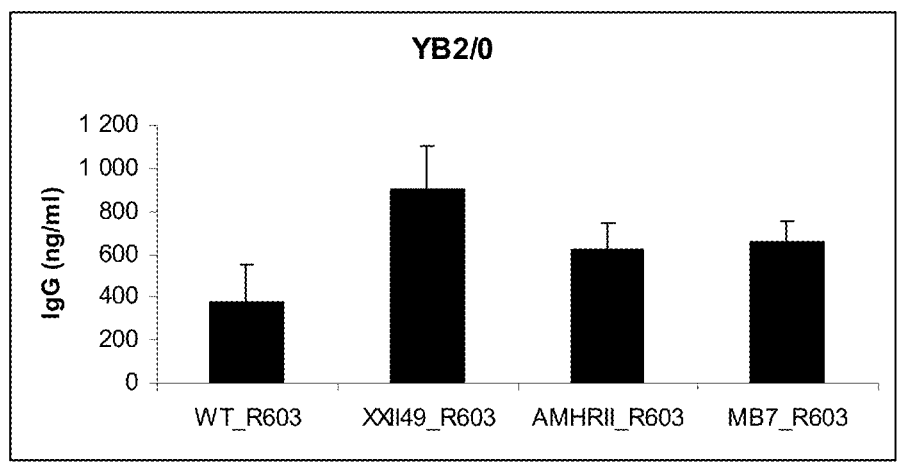

FIG. 4 shows a comparison of the effect of 3 signal peptides, including 12G4, XXII49 and MB7, on the secretion of a whole anti-CD20 antibody (R603), in the YB2/0 cell line evaluated in transient transfection. The four columns, from left to right, represent respectively the secretion rate of the R603 antibody bound respectively to its initial signal peptides (heavy chain, light chain), to the signal peptide 12G4, to the signal peptide XXII49 and to the signal peptide according to the invention MB7. The y-axis represents the concentration of R603 antibody secreted in the culture medium.

Figure 5:
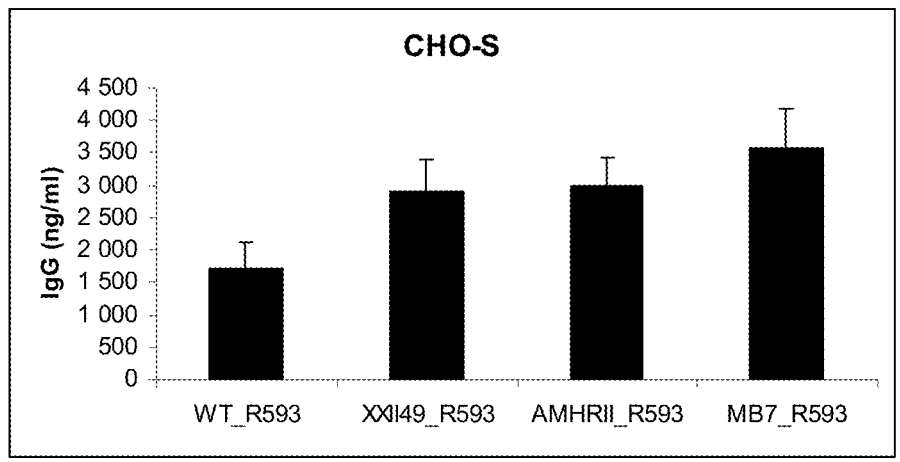

FIG. 5 shows a comparison of the effect of 3 signal peptides, including 12G4, XXII49 and MB7, on the secretion of a whole anti-RhD antibody (R593), in the CHO-S cell line evaluated in transient transfection. The four columns, from left to right, represent respectively the secretion rate of the R593 antibody bound respectively to its initial signal peptides (heavy chain, light chain), to the signal peptide 12G4, to the signal peptide XXII49 and to the signal peptide according to the invention MB7. The y-axis represents the concentration of R593 antibody secreted in the culture medium.

Figure 6:
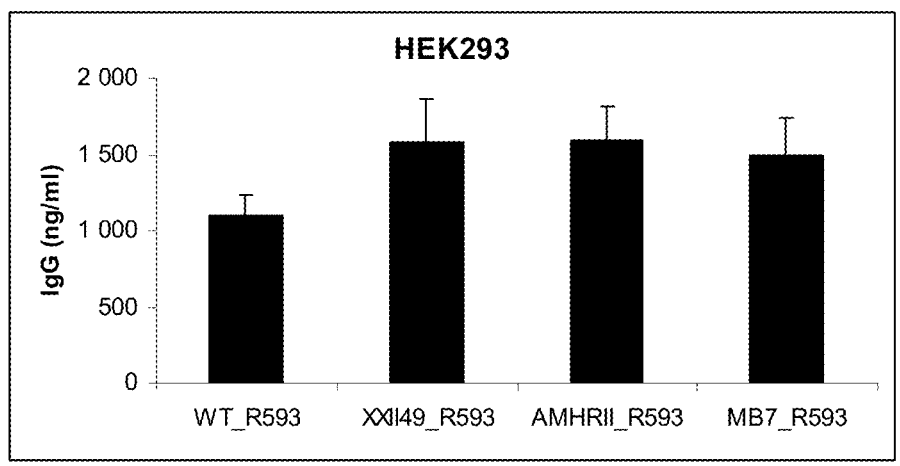

FIG. 6 shows a comparison of the effect of 3 signal peptides, including 12G4, XXII49 and MB7, on the secretion of a whole anti-RhD antibody (R593), in the cell line HEK293 evaluated in transient transfection. The four columns, from left to right, represent respectively the secretion rate of the R593 antibody bound respectively to its initial signal peptides (heavy chain, light chain), to the signal peptide 12G4, to the signal peptide XXII49 and to the signal peptide according to the invention MB7. The y-axis represents the concentration of R593 antibody secreted in the culture medium.

Figure 7:
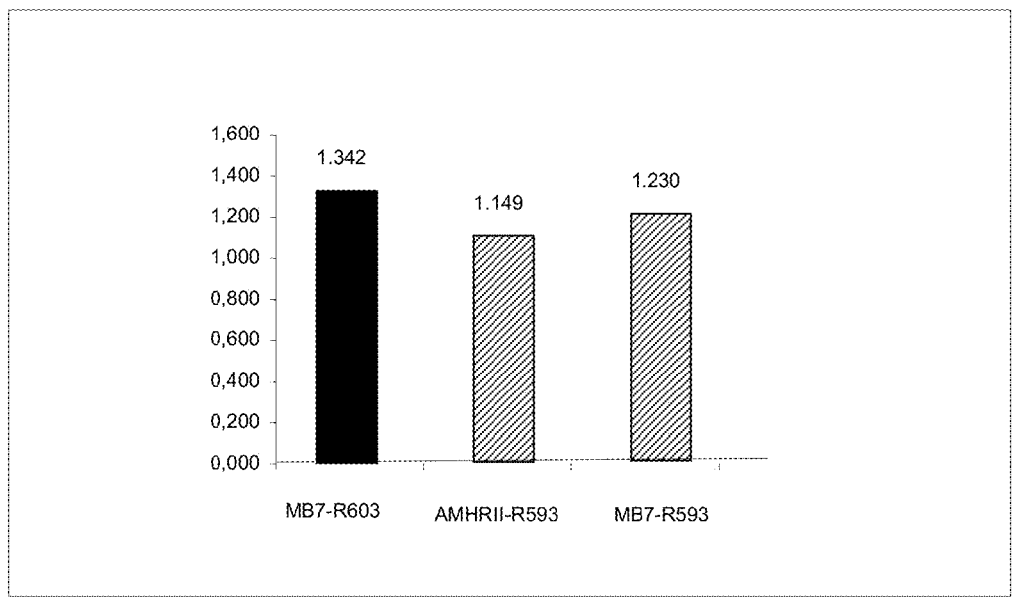

FIG. 7 shows the comparison of the average productions as a function of the different signal peptides with respect to the natural signal peptides in the PER.C6 cell line. The y-axis represents the ratio between the secretion rate of the antibody bound to a signal peptide according to the invention (12G4 or MB7) and the secretion rate of the antibody bound to its natural signal peptides. The three columns, from left to right, represent respectively the secretion rate of the R603 antibody bound to the signal peptide MB7, and the secretion rate of the R593 antibody bound respectively to the signal peptide 12G4, and to the signal peptide MB7.

Figure 8A:
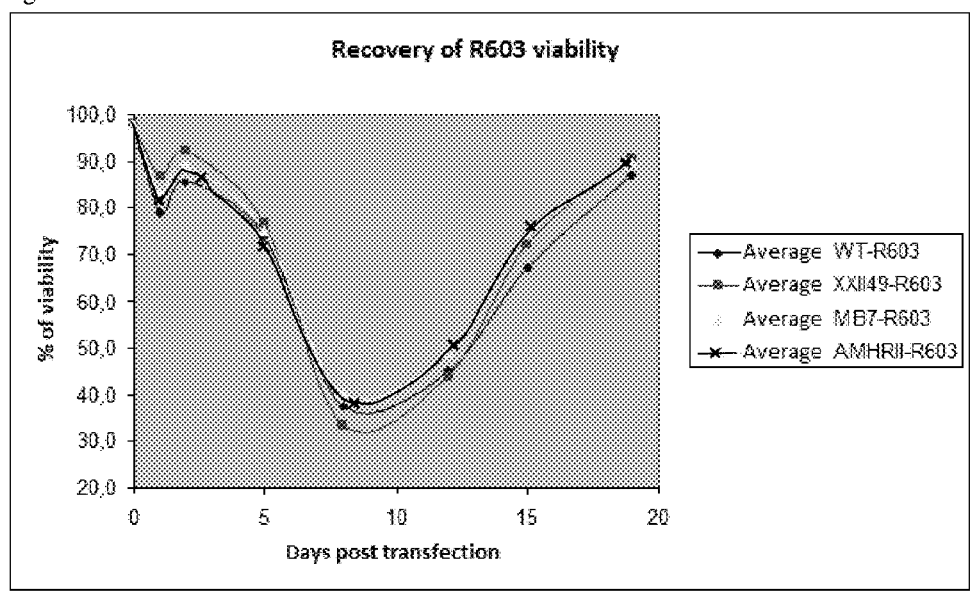

FIG. 8A shows the recovery of viability after transfection for the anti-CD20 bound respectively to its natural signal peptide (diamond), to the signal peptide XXII49 (square), to the signal peptide MB7 (triangle), and to the signal peptide 12G4 (cross). The y-axis represents the percentage of viability. The x-axis represents the days post transfection. The results are the average of the three stable pools.

FIG. 8A shows the recovery of viability after transfection for the anti-Rh(D) bound respectively to its natural signal peptide (diamond), to the signal peptide XXII49 (square), to the signal peptide MB7 (triangle), and to the signal peptide 12G4 (cross). The y-axis represents the percentage of viability. The x-axis represents the days post transfection. The results are the average of the three stable pools.

EXAMPLES

Example 1

Materials and Methods 1.1 Peptide Signals Analyzed

Seven signal peptides respectively originating from a polypeptide chain naturally bearing a signal peptide are chosen by the Inventors in order to analyze the secretory power of these 7 different signal peptides.

These 7 polypeptide chains are respectively the gamma chain of an anti-AMHRII antibody (12G4, 1-3673 CNCM) the gamma chain of an anti-CD5 antibody (XXII49, unpublished data), the gamma chain of an anti-RhD antibody (D29, FR 2861078), the gamma chain of a anti-LDL receptor (5E5, I-3488 CNCM), the kappa chain of an anti-CD20 antibody (Cat13, supplier: DSMZ, ref. ACC 474), the α chain of the TCR receptor of $T^2$ lymphocytes (HAVT20, Genbank accession number H32536) and the human erythropoietin (EPO, Genbank accession number AAI43226).

The secretory power of a signal peptide is evaluated according to two aspects, namely its directing ability and ability to be cleaved.

Descriptions and predictions of the secretory power of a signal peptide are analyzed beforehand (Emanuelsson et al., *Nature Protocols* 2, 953-971 (2007)).

The signal peptides (SP) were subjected to the algorithm SignalP V3.0 in the form of SP fusion protein/light chain of the anti-Rh(D) antibody T125 (FR2807767).

1.2 Construction of the Expression Vectors for the Evaluation of the SP on the Expression of the Light Chain of the Anti-Rh(D) Antibody T125

The method is identical for each SP, it breaks down into two PCR series. A first PCR is carried out with the primers P1 and P2, which allow the synthesis of the 40 to 50 bases of the SP and the integration of the NheI site at the 5' end of the sequence. A second PCR is carried out in parallel with the primers P3 and P2_Kappa_XbaI and the plasmid RSV-int_KT125 2stp as a matrix. It will subsequently allow the joining of the SP to the kappa chain and integration of the XbaI cloning site into the 3' end. A third PCR is then carried out. This assembly PCR is carried out with the primers P1 and P2_Kappa_XbaI (FIG. 1).

In order to limit nucleotide incorporation errors, the Proofreading enzyme (proofstart Taq, Qiagen) is used for the DNA amplification, and the number of cycles is limited.

The PCRs are carried out under the following conditions:

Activation enzyme 94° C., 5 minutes
Denaturation 94° C. 15 sec ⎫
Hybridization 52° C. 30 sec ⎬ 15 cycles
Extension 72° C. 1.5 min ⎭
Final extension 72° C. 2 min (thank you for completing this part)

The primers used are given below:

For the construction of the fusion chain SP(12G4)/kappa (T125)

```
P1_12G4
                                          (SEQ ID NO: 5)
5'-CTCTTGCTAGCGCCGCCACCATGCGATGGAGCTGGATCTT-3'

P2_12G4
                                          (SEQ ID NO: 6)
5'-CACTTGCAGTTATTGACAGGAGGAAGAGAAAGATCCAGCT-3'

P3_12G4
                                          (SEQ ID NO: 7)
5'-ACTGCAAGTGTCCATTGCGCCATCCGGATGACCCAGTCTC-3'
```

For the construction of the fusion chain SP(XXII49)/kappa (T125)

```
P1_XXII49
                                          (SEQ ID NO: 8)
5'-CTCTTGCTAGCGCCGCCACCATGGCTTGGGTGTGGACCTT-3'

P2_XXII49
                                          (SEQ ID NO: 9)
5'-CACTTTGGGCAGCTGCCATCAGGAATAGCAAGGTCCACAC-3'

P3_XXII49
                                          (SEQ ID NO: 10)
5'-GCCCAAAGTGCCCAAGCAGCCATCCGGATGACCCAGTCTC-3'
```

For the construction of the fusion chain SP(D29)/kappa (T125)

P1_D29
(SEQ ID NO: 11)
5'-CTCTTGCTAGCGCCGCCACCATGGAGCTTGGGCTGAGCTG-3'

P2_D29
(SEQ ID NO: 12)
5'-ACACCTCTTAAAAGAGCAACGAGAAAAACCCAGCTCAGCCC-3'

P3_D29
(SEQ ID NO: 13)
5'-TTAAGAGGTGTCCAGTGTGCCATCCGGATGACCCAGTCTC-3'

For the construction of the fusion chain SP(5E5)/kappa (T125)

P1_5E5
(SEQ ID NO: 14)
5'-CTCTTGCTAGCGCCGCCACCATGGGTTGGAGCTGTATCAT-3'

P2_5E5
(SEQ ID NO: 15)
5'-ACACCTGTAGCTGTTGCTACCAGAAAGAAGATGATACAGCTC-3'

P3_5E5
(SEQ ID NO: 16)
5'-AGCTACAGGTGTGCACTCCGCCATCCGGATGACCCAGTCTC-3'

For the construction of the fusion chain SP(CAT13)/kappa (T125)

P1_CAT13 (SEQ ID NO: 17):
5'-CTCTTGCTAGCGCCGCCACCATGGATTTTCAAGTGCAGATTTTC-3'

P2_CAT13 (SEQ ID NO: 18):
5'-CATTATGACTGAAGCACTGATTAGCAGGAAGCTGAAAATCTGCAC-3'

P3_CAT13 (SEQ ID NO: 19):
5'-CTTCAGTCATAATGTCCAGAGGAGCCATCCGGATGACCCAGTCTC-3'

For the construction of the fusion chain SP(EPO)/kappa (T125)

P1_EPO(H) (SEQ ID NO: 20):
5'-CTCTTGCTAGCGCCGCCACCATGGGGGTGCACGAATGTCCTGCCTGGCTG-3'

P2_EPO(H) (SEQ ID NO: 21):
5'-CAGAGGGAGCGACAGCAGGGACAGGAGAAGCCACAGCCAGGCAGGA-3'

P3_EPO(H) (SEQ ID NO: 22):
5'-TCGCTCCCTCTGGGCCTCCCAGTCCTGGGCGCCATCCGGATGACCCAGTCTC-3'

For the construction of the fusion chain SP(HAVT20)/kappa(T125)

P1_HAVT20 (SEQ ID NO: 23):
5'-CTCTTGCTAGCGCCGCCACCATGGCATGCCCTGGCTTCCTGT-3'

P2_HAVT20 (SEQ ID NO: 24):
5'-AATTCAAGACAGGTGGAGATCACAAGTGCCCACAGGAAGCCAG-3'

P3_HAVT20 (SEQ ID NO: 25):
5'-CCTGTCTTGAATTTTCCATGGCTGCCATCCGGATGACCCAGTCTC-3'

P2_KAPPA_Xba1 (SEQ ID NO: 26):
5'-GCGAGCTCTAGAGTTCACTAACACTCTCCCCTGTTGAAGCTC-3'

The vector RSV-int_KT125 2stp is digested by NheI and XbaI. A fragment of 725 bases, corresponding to the nucleotide sequence encoding the light chain of T125, is removed. A fragment of 5028 bases is recovered. The PCR product thus prepared is also digested by NheI and XbaI. The fragments after digestion are recovered and purified by Nuleospin® Extract (Clonetech). The PCR product thus digested is cloned between the NheI and XbaI sites in the expression vector RSV-int KT125-2stp in place of the light chain already present. The correct insertion of the PCR product is verified by a PCR using two primers: P1 and P2_KAPPA_Xba1. An amplicon of approximately 750 to 760 bases following the signal peptides must be obtained, when the vector is constructed correctly. The correct insertion of the PCR product into the vector is also verified by the sequencing using the primer 2BGHPA represented by the sequence SEQ ID NO: 27 (5'-CAGATGGCTGGCAACTAGAA-3').

1.3 Construction of the Expression Vectors for the Evaluation of the SP on the Expression of the Anti-Rh(D) Antibody T125 and Anti-CD20 Antibody On the same principle as previously (section 1.2), the SP of the anti-AMHRII, anti-CD5, and artificial SP MB7 are added to the heavy and light chains of the anti-Rh(D) antibody T125 and anti-CD20 antibody by assembly PCR (Table 3), conventional PCR (Table 2) or simple cloning (Table 1) of the fragments generated in the first part of the study according to the tables below:

TABLE 1

| Chains | | | | | Final vector |
|---|---|---|---|---|---|
| Name | Vector | Enzyme1 | Enzyme2 | Size (bp) | name |
| K_WT_R593 | RSV_int_KT125_2STP | NheI | XbaI | 725 | WT_R593 |
| K_XXII49_R593 | RSV_PSG_XXII49_KT125 | NheI | XbaI | 722 | XXII49_R593 |
| K_AMHRII_R593 | RSV_PSG_AMHRII_KT125 | NheI | XbaI | 722 | AMHRII_R593 |

TABLE 2

| Chains | | | | | Final vector |
|---|---|---|---|---|---|
| Name | Vector | Primer1 | Primer2 | Size (bp) | name |
| H_WT_R593 | HK463-18-9 | P1_NheI_H_R593 | GSP2ANP | 555 | WT_R593 |
| K_WT_R603 | HK463-25 | P1_CAT13 | CK4 | 509 | WT_R603 |

TABLE 3

| vector | chain | PCR1 5' primer | PCR1 3' primer | amplicon1 size (bp) | Assembly PCR3 / PCR2 5' primer | PCR2 3' primer | amplicon2 size (bp) | final size (bp) | taille after digestion (bp) |
|---|---|---|---|---|---|---|---|---|---|
| XXII49_R603 | heavy chain | P1_XXII49 | P2_XXII49 | 69 | P3_XXII49_H_R603 | GSP2ANP | 472 | 531 | 441 |
|  | light chain |  |  |  | P3_XXII49_K_R603 | CK4 | 441 | 500 | 408 |
| AMHRII_R603 | heavy chain | P1-AMHRII | P2-AMHRII | 69 | P3_AMHRII_H_R603 | GSP2ANP | 472 | 531 | 441 |
|  | light chain |  |  |  | P3_AMHRII_K_R603 | CK4 | 441 | 500 | 408 |
| MB7_R603 | heavy chain | P1-AMHRII | P2_MB7 | 63 | P3_MB7_H_R603 | GSP2ANP | 475 | 528 | 438 |
|  | light chain |  |  |  | P3_MB7_K_R603 | CK4 | 444 | 497 | 405 |
| XXII49_R593 | heavy chain | P1_XXII49 | P2_XXII49 | 69 | P3_XXII49_H_R593 | GSP2ANP | 496 | 555 | 465 |
| AMHRII_R593 MB7_R593 | heavy chain | P1-AMHRII | P2-AMHRII | 69 | P3_AMHRII_H_R593 | GSP2ANP | 496 | 555 | 465 |
|  | heavy chain | P1-AMHRII | P2_MB7 | 63 | P3_MB7_H_R593 | GSP2ANP | 499 | 552 | 462 |
|  | light chain |  |  |  | P3_MB7_K_R593 | P2_Kappa_XbaI | 683 | 736 | 719 |

Each heavy and light chain pair fused with an SP to be evaluated is then cloned in the vector HK463-25 sequentially according to the diagram of FIG. 2A or FIG. 2B. The variable part of each light chain is amplified according to the above tables, is then digested by NheI/DraIII before ligation in the vector, itself digested by SpeI/DraIII. A screening by PCR and enzymatic digestion is then carried out in order to identify the bacterial clones resulting from the transformation with the vector. The correctly generated clones are then manipulated in order to insert the variable part of the heavy chain. This is done by NheI/ApaI digestion of the vector and of the PCR product before ligation, bacterial conversion and screening in order to identify the bacterial clones in compliance.

The different vectors thus constructed were then evaluated in transient transfection in YB2/0, PER.C6, CHO-S and HEK or in stable transfection in the lines YB2/0 and PER.C6.

1.4 Transient Transfection

In the case of YB2/0, the parent cells are seeded the day before the transfection (D-1) at $2^E5$ cv/ml in EMS (Invitrogen, medium made up)+5% FCS (Invitrogen) in a flask. On the day of the electroporation (DO), centrifugation of $4^E6$ cells per 4-mm cuvette (Biorad) taken up in 100 µl of buffer V (Cell line nucleofector kitV, Lonza) which are nucleofected by AMAXA with 4 µg of plasmid DNA using program T020 of the device. The cells are cultured in P6 plate wells at 37° C., 7% $CO_2$ in 3 ml of EMS medium+5% FCS. The supernatants are collected for ELISA assay on D+5.

In the case of adherent PER.C6, the parent cells are seeded 24 hours before transfection (D-1) in 24-well plates at $1^E6$ cv/ml in DMEM (Fisher Bioblck Scientific)+10% FCS. On the day of the transfection a FuGENE® HD (Roche)/DNA complex, in a ratio of 6:2, is formed in DMEM over 15 min at ambient temperature. The complex (25 µl) is then deposited on the cells in the presence of 250 µl of DMEM+10% fresh FCS and incubated for 4 hours at 37° C. and 10% of $CO_2$. At the end of this period, 250 µl of complete medium is added and the supernatants are collected on D+5 for evaluation of molecule secreted in the medium.

In the case of CHO-S, the SPs are evaluated in transient transfection according to the FreeStyle kit protocol (Invitrogen). The parent cells are seeded 24 hours before transfection (D-1) in an Erlenmeyer flask (VWR) at $6^E5$ cells/ml in FreeStyle CHO EM (Fisher Bioblock scientific) and incubated at 120 rpm at 37° C., 8% $CO_2$. On the day of the transfection a FreeStyle MAX Reagent (Fisher Bioblock Scientific)/DNA complex, in a ratio of 1:1, is formed in Opti Pro SFM (Invitrogen). The complex is then deposited on the previously centrifuged cells in suspension and taken up at $1^E6$ c/ml in FreeStyle CHO EM in a cultiflask (Sartorius) (5 ml) and incubated at 200 rpm at 37° C., 8% of $CO_2$. The supernatants are collected on D+5 for evaluation of the number of molecules secreted in the medium.

In the case of HEK293F, the SPs are evaluated in transient transfection according to the FreeStyle kit protocol (Invitrogen). The parent cells are seeded 24 hours before the transfection (D-1) in an Erlenmeyer flask at $6^E5$ cv/ml in F17 293 EM medium (Fisher Bioblock Scientific) and incubated at 120 rpm at 37° C., 8% $CO_2$. On the day of the transfection a 293Fectin/DNA complex, in a ratio of 2:1, is formed in Opti Pro SFM. The complex is then deposited on the previously centrifuged cells and taken up at $1^E6$ c/ml in F17 293 EM and incubated at 200 rpm at 37° C., 8% of $CO_2$. The supernatants are collected on D+5 for evaluation of the level of molecules secreted in the medium.

1.5 Stable Transfection

The evaluations are carried out on pools of transfectants ("stable transfection pools") in order to compare the different constructions on the basis of a level of expression averaged over a large number of transfectants (several thousand).

In the case of YB2/0, the transfections in stable pools are carried out as follows:

The cells must have a stabilized growth and have been thawed for at least 4 weeks in EMS medium+5% FCS in an F150 flask (80 ml). The cells are sub-cultured the day before at $2^E5$ cv/ml in EMS medium+5% FCS.

On the day of the electroporation, the cells are electroporated by a Gene Pulser Xcell system (BioRad) with a voltage of 230V and capacitance of 960 µF in 4-mm cuvettes (Biorad) with $5^E6$ cv (qsf 500 µl of electroporation buffer from the electrobuffer kit (Ozyme) containing the linearized plasmid DNA). After electroporation plating is carried out on 24-well plates (P24) (25000 cells/well) in EMS medium+5% FCS.

On D+3: Placed in selective medium in order to obtain the following final concentrations: EMS+5% FCS+G418 1 g/l+1% phenol red.

On D+7: Renewal of the plates with the corresponding medium.

On D+10: When the wells exhibit significant growth, make 3 P24 pools of 8 wells, sub-culture the cells at $2^E5$ cv/ml in F25 and carry out maximum production (Max prod on D+7), the supernatant is collected and assayed using FastELYSA.

In the case of PER.C6, the parent cells used are adapted PERC6SF cells in Permab medium (ThermoFisher) and cultured for 3 weeks under stirring at 100 rpm. Two days before electroporation, the sub-cultured cells are transferred to $5^E5$ cv/ml by a complete change of the Permab medium. On the day of the electroporation, each pool is prepared by 5 electroporations in 4-mm cuvettes for $6^E6$ cv with 8 µg of linearized plasmid DNA. The cells are electroporated by Gene Pulser Xcell (BioRad) according to the manufacturer's instructions.

48 hours after the transfection, the selection pressure (G418 at 125 µg/ml) is applied to the cells which are kept in culture for approximately 4 to 5 weeks, adapting the volume of culture in order to keep a concentration of $3^E5$ cv/ml at each pass. After cell viability drops to 20%, the cells are subjected to stirring. When the viability reaches approximately 50% and at 85%, an evaluation of the productivity of the pool is carried out on cultures in batches on D+7.

For each construction, 3 different pools are carried out by cell line and analyses. The productions in pools are expressed in ng/ml.

1.6 Evaluation of the Level of Recombinant Protein Secreted

Evaluation of the free kappa chain level of the anti-Rh(D) antibody T125 as well as the production of IgG1, of anti-CD20 or of anti-Rh(D) T12 are determined by the Enzyme-Linked Immunosorbent Assay (ELISA) technique.

The free kappa chain present in the culture supernatant is captured over 2 hours by a goat anti-human kappa antibody (Caltag Lab) which is adsorbed on 96-well plates. The captured antibody is then developed by a biotinylated goat anti-human kappa antibody (Pierce) followed by addition of streptavidin coupled to peroxidase (Pierce). Between each stage 4 washes are carried out to remove the less reactive proteins not included in the complex. The development is carried out by adding the enzyme substrate, PD (Sigma) and stopping the reaction with 1N HCl. The reading is carried out with a spectrophotometer at 492 nm. The antibody concentration of determined in comparison with a standard range.

The IgG1s produced in transient and stable transfection are evaluated by the Fast ELYSA kit (RD-biotech) according to the supplier's instructions. The optical density is read with a spectrophotometer at 450 nm. The antibody concentration is determined in comparison with a standard range contained in the kit.

A comparison is carried out between the kappa chain of the anti-Rh(D) antibody T125 secreted by the signal peptides according to the invention and that secreted by its natural signal peptide.

A comparison is also carried out between the anti-Rh(D) antibody T125 or the anti-CD20 antibody produced using at least one of the signal peptides according to the invention and that produced by the natural signal peptides of each of the antibodies respectively.

The natural signal peptide of the light chain of the anti-Rh (D) antibody T125 is encoded by the nucleic acid SEQ ID NO: 30 (atgagggtccccgctcagctc-ctggggctcctgctgctctggctcccaggtgccagatgt).

The natural signal peptide of the heavy chain of the anti-Rh(D) antibody T125 is encoded by the nucleic acid SEQ ID NO: 31 (atggagtttgggctgagctgggttttc-ctcgttgctcttttaagaggtgtccagtgt).

The natural signal peptide of the light chain of the anti-CD20 antibody is encoded by the nucleic acid SEQ ID NO: 32 (atggattttcaagtgcagattttcagct-tcctgctaatcagtgcttcagtcataatgtccagagga).

The natural signal peptide of the heavy chain of the anti-CD20 antibody is encoded by the nucleic acid SEQ ID NO: 33 (atgggattcagcaggatctttctcttcctcctgtcagtaactacaggtgtccactcc).

Example 2

In Vitro Evaluation of the Signal Peptides on the Secretion of an Antibody Light Chain The secretory power of these 7 signal peptides is tested in vitro in transient transfection in the lines PER.C6, CHO-S, YB2/0. The method of transient transfection is described in the section above (see Section 1.2).

2.1 Effect of 7 Signal Peptides in the Line PER.C6

The results obtained from the 4 transient transfections carried out over 4 different weeks make it possible to observe significant differences between the SPs.

A multiple comparison is carried out for the Ig light chain production averages (ng/mL) obtained with the different signal peptides in the line PER.C6 (Table 4). The method currently used to discriminate between the averages is the Fisher's Least Significant Difference (LSD) procedure. Multiple range tests are carried out with the 95.0% LSD method. These pairs have statistically significant differences at the 95.0% confidence level.

TABLE 4

|  | Effective | Average | Homogeneous group |
|---|---|---|---|
| EPO_h | 16 | 3828.92 | X |
| PSK_CAT13 | 16 | 3834.16 | X |
| HAVT20 | 16 | 3985.15 | X |
| PSG_12G4 | 16 | 4468.87 | XX |
| PSG_5E5 | 16 | 5207.61 | XX |
| PSG_D29 | 16 | 5563.95 | X |
| PSG_XXII49 | 16 | 5696.46 | X |

Two homogeneous groups are identified using columns of Xs. In each column, the levels containing Xs form a group of averages within which there are no statistically significant differences. The signal peptides of the heavy chains of the antibodies XXII49 and D29 are significantly more effective in the production of the Ig (anti-Rh(D)) light chain than the SP of the antibody Cat13 (anti-CD20), of HAVT20, and of EPO.

The differences in production obtained between the different SPs are only slight. Nevertheless, the SPs of the heavy chains of the antibody XXII49 and of the antibody D29 differ from each other in the line PER.C6, with a slight advantage for that of the antibody XXII49. The three least good peptides are those of the antibody Cat13, of HAVT20, and of EPO.

2.2 Effect of 7 Signal Peptides in the Line YB2/0

The results obtained from the 5 transfections carried out over 5 different weeks make it possible to observe significant differences between the SPs.

A multiple comparison is carried out for the Ig light chain production averages (ng/mL) obtained with the different signal peptides in the line YB2/0 (Table 5). The method currently used to discriminate between the averages is the Fisher's Least Significant Difference (LSD) procedure. Multiple range tests are carried out with the 95.0% LSD method. These pairs have statistically significant differences at the 95.0% confidence level.

TABLE 5

|  | Effective | Average | Homogeneous group |
|---|---|---|---|
| PSK_CAT13 | 20 | 2744.26 | X |
| HAVT20 | 20 | 3181.69 | XX |
| EPO_h | 20 | 3479.19 | XXX |
| PSG_5E5 | 20 | 3756.33 | XX |
| PSG_D29 | 20 | 4255.05 | XX |
| PSG_12G4 | 20 | 5131.64 | XX |
| PSG_XXII49 | 20 | 5372.39 | X |

Five homogeneous groups are identified using columns of Xs. The SP of the heavy chain of the antibody XXII49 is significantly more effective than all the other peptides except for that of 12G4. On the other hand, the SP of the light chain of the anti-CD20 (Cat13) appears to be the least good of the SPs with those of HAVT20, and of EPO.

The SPs of the heavy chains of the antibodies XXII49, 12G4, and D29 appear to be the best SPs with that of the XXII49 having the advantage. The three least good peptides are those of the antibody Cat13, of HAVT20, and of EPO, as observed previously in the line PER.C6.

2.3 Effect of 7 Signal Peptides in the Line CHO-S

The results obtained from the 4 transfections carried out over 4 different weeks make it possible to observe significant differences between the SPs.

A multiple comparison is carried out for the Ig light chain production averages (ng/mL) obtained with the different signal peptides in the line CHO-S (Table 6). The method currently used to discriminate between the averages is the Fisher's Least Significant Difference (LSD) procedure. Multiple range tests are carried out with the 95.0% LSD method. These pairs have statistically significant differences at the 95.0% confidence level.

TABLE 6

|  | Effective | Average | Homogeneous group |
|---|---|---|---|
| EPO_h | 16 | 8210.98 | X |
| HAVT20 | 16 | 9297.38 | X |
| PSK_CAT13 | 16 | 10345.3 | XX |
| PSG_D29 | 16 | 10994.3 | XX |
| PSG_5E5 | 16 | 13399.1 | XX |
| PSG_12G4 | 16 | 14156.1 | X |
| PSG_XXII49 | 16 | 14720.1 | X |

Three homogeneous groups are identified using columns of Xs. The SP of the heavy chain of the antibody XXII49 is significantly more effective than those of the antibodies D29, Cat13, of HAVT20 and of EPO. On the other hand, its secretory power is similar to those of the heavy chains of the antibodies 12G4 and 5E5.

The SPs of the heavy chains of the antibodies XXII49 and 12G4 are the best SPs with that of the XXII49 having the advantage. The three least good peptides are those of the antibody Cat13, of HAVT20 and of EPO, as observed previously in the lines PER.C6 and YB2/0.

Example 3

In Vitro Validation of the Signal Peptides on the Secretion of a Whole Immunoglobulin The best two SPs identified (XXII49 and 12G4) in silico and in vitro as well as an artificial SP according to the invention, MB7, were tested in order to evaluate the potential gain in productivity of whole antibodies that could provide these SPs fused to the heavy and light chains of immunoglobulins. The antibodies tested are anti-Rh(D) (R593) and anti-CD20 (R603). The different molecules were tested in transient transfection in the lines PER.C6, YB2/0, CHO-S and HEK then on stable pools in PER.C6 and YB2/0.

The method of transient transfection as well as that of stable transfection in each line in question are described in the abovementioned sections (see 1.4 and 1.5).

3.1 Effect of the Signal Peptides in the Line PER.C6

3.1.1 Transient Transfections

The results obtained from the 4 transient transfections carried out over 4 different weeks make it possible to observe significant differences between the SPs.

The average secretion of the R593 antibody using the signal peptide MB7 according to the invention is increased by a factor of 1.80 relative to that of the R593 antibody bound to its own signal peptide. The signal peptide 12G4 and the signal peptide XXII49 also make it possible to increase the secretion rate of the R593 antibody in the line PER.C6 by a factor of 1.71 and 1.58 respectively. (FIG. 3 and Table 7).

TABLE 7

|  | Effective | Average | Homogeneous group |
|---|---|---|---|
| WT_R593 | 12 | 425.03 | X |
| XXII49_R593 | 12 | 672.51 | X |
| 12G4_R593 | 12 | 727.532 | XX |
| MB7_R593 | 11 | 766.072 | X |

In Table 7, the method currently used to discriminate between the averages is the Fisher's Least Significant Difference (LSD) procedure. Multiple range tests are carried out with the 95.0% LSD method. These pairs have statistically significant differences at the 95.0% confidence level.

3.1.2. Stable Transfections

PER.C6 cells were transfected for the generation of stable pools as described in Section 1.5. These transfections were repeated over 3 weeks in order to be compared with the results obtained in transient transfection.

The results are shown in Table 8 and FIG. 7.

In Table 8, the method currently used to discriminate between the averages is the Fisher's Least Significant Difference (LSD) procedure. Multiple range tests are carried out with the 95.0% LSD method. These pairs have statistically significant differences at the 95.0% confidence level.

TABLE 8

|  | Effective | Average | Homogeneous group |
|---|---|---|---|
| WT_R603 | 6 | 1708.87 | X |
| MB7_R603 | 6 | 2293.53 | X |
| WT_R593 | 6 | 4576.45 | X |
| 12G4_R593 | 6 | 5258.34 | X |
| MB7_R593 | 6 | 5629.72 | X |

A batch production was carried out over 7 days on the three stable pools and the samples were assayed by FastELYSA. The results of the production on D+7 were statistically analyzed in order to compare the effect of the signal peptides on the secretion of IgG1. The statistical analysis shows a significant difference between the signal peptide MB7 and the natural peptides (WT), both for the anti-CD20 antibody (R603) and for the anti-Rh(D) (R593) (Table 8).

For the anti-Rh(D) antibody, the signal peptide 12G4 (heavy chain) also shows an average significantly different from that of the natural signal peptides (WT).

FIG. 7 shows the ratio of the average productions between the optimized and natural signal peptides. A level of production is observed, which is a factor of 1.3 greater in the case of MB7-R603 and a factor of 1.2 greater in the case of MB7-R593. This therefore shows that the signal peptide MB7 provides a real gain in productivity.

For the anti-Rh(D) antibody containing the signal peptide 12G4, the significant difference in average shown by the multiple range test is reflected in productivity increased by a factor of 1.15.

Figure 8B:
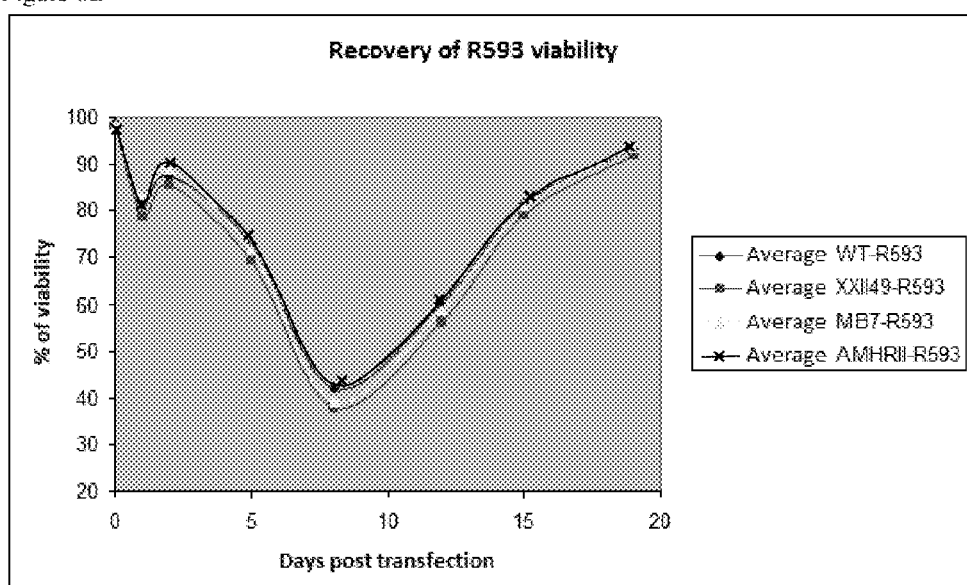

The effect of the signal peptides on cell viability was also studied for the production of the anti-CD20 antibody (R603) (FIG. 8A) or the production of the anti-Rh(D) antibody (R593) (FIG. 8B), in the PER.C6 cell line. For the anti-CD20 antibody (R603), it is observed that recovery of viability after transfection and the addition of selection pressure takes place slightly more rapidly in the presence of the signal peptide MB7 than in the presence of the natural peptides. This provides a slight gain in time in the establishment of the stable pool as the cells containing the MB7 can be re-subjected to stirring 1 to 2 days before the cells containing the natural signal peptides. The anti-CD20 antibody accumulates in the cell and produces a toxic effect on the cell. The signal peptide MB7, by increasing the secretion of the antibody, reduces this toxic effect and therefore thus promotes the recovery of the cells. This effect is not observed with the anti-Rh(D) antibody which has better productivity than the anti-CD20 and is therefore not subjected to this toxicity by accumulation of the antibody in the cell (FIG. 8B).

3.2 Effect of the Signal Peptides in the Line YB2/0

3.2.1 Transient Transfections

The results obtained from the 3 transient transfections carried out over 3 different weeks make it possible to observe significant differences between the SPs (Table 9).

TABLE 9

|  | Effective | Average | Homogeneous group |
|---|---|---|---|
| 12G4_R603 | 12 | 618.756 | X |
| MB7_R603 | 12 | 656.243 | X |
| XXII49_R603 | 12 | 904.177 | X |
| WT_R603 | 12 | 374.04 | X |

In Table 9, the method currently used to discriminate between the averages is the Fisher's Least Significant Difference (LSD) procedure. Multiple range tests are carried out with the 95.0% LSD method. These pairs have statistically significant differences at the 95.0% confidence level.

The average secretion of the R603 antibody using the peptide MB7 according to the invention is increased by a factor of 1.75 relative to that of the R603 antibody bound to its own signal peptide (FIG. 4). The signal peptide 12G4 and the signal peptide XXII49 also make it possible to increase the secretion rate of the R603 antibody in the line YB2/0 by a factor of 1.65 and 2.42 respectively.

3.2.2 Stable Transfections

The YB2/0 cells were transfected for the generation of stable pools as described in Section 1.5. These transfections were repeated over 3 weeks in order to be compared with the results obtained in transient transfection.

A batch production was carried out over 7 days on the three stable pools and the samples were assayed by FastELYSA.

The results of the production on D+7 were statistically analyzed in order to compare the effect of the signal peptides on the secretion of IgG1.

The signal peptide MB7 gives the same level of productivity of the R603 antibody in the YB2/0 cells as that of its natural signal peptide.

3.3 Effect of the Signal Peptides in the Line CHO-S

The results obtained from the 3 transient transfections carried out over 3 different weeks make it possible to observe significant differences between the SPs (Table 10).

TABLE 10

|  | Effective | Average | Homogeneous group |
|---|---|---|---|
| XXII49_R593 | 12 | 2902.13 | X |
| 12G4_R593 | 10 | 2984.74 | X |
| MB7_R593 | 10 | 3570.06 | X |
| WT_R593 | 10 | 1702.78 | X |

In Table 10, the method currently used to discriminate between the averages is the Fisher's Least Significant Difference (LSD) procedure. Multiple range tests are carried out with the 95.0% LSD method. These pairs have statistically significant differences at the 95.0% confidence level.

The average secretion of the R593 antibody using the peptide MB7 according to the invention is increased by a factor of 2.1 relative to that of the R593 antibody bound to its own signal peptide (FIG. 5). The signal peptide 12G4 and the signal peptide XXII49 also make it possible to increase the secretion rate of the R593 antibody in the line CHO-S by a factor of 1.75 and 1.7 respectively.

3.4 Effect of the Signal Peptides in the Line HEK293

The results obtained from the 3 transient transfections carried out on 3 different weeks make it possible to observe significant differences between the SPs (Table 11).

TABLE 11

|  | Effective | Average | Homogeneous group |
|---|---|---|---|
| MB7_R593 | 12 | 1490.05 | X |
| XXII49_R593 | 12 | 1578.98 | X |
| 12G4_R593 | 12 | 1598.12 | X |
| WT_R593 | 12 | 1099.81 | X |

In Table 11, the method currently used to discriminate between the averages is the Fisher's Least Significant Difference (LSD) procedure. Multiple range tests are carried out with the 95.0% LSD method. These pairs have statistically significant differences at the 95.0% confidence level.

The average secretion of the R593 antibody using the peptide MB7 according to the invention is increased by a factor of 1.35 relative to that of the R593 antibody bound to its own signal peptide (FIG. 6). The signal peptide 12G4 and the signal peptide XXII49 also make it possible to increase the secretion rate of the R593 antibody in the line HEK 293 by a factor of 1.45 and 1.44 respectively.

3.5 Effect of the Change of Signal Peptide on the Primary Structure of the Molecule Produced.

In order to see whether the change of signal peptide has any impact on the primary structure of the secreted antibody, physicochemical analyses by mass spectrometry and N-terminal sequencing by the Edman technique at the level of the heavy and light chains of the anti-Rh(D) and the anti-CD20 products in YB2/0 and PER.C6 were carried out in stable transfection.

The mass spectrometry results summarized in Table 12 show that the masses observed for the 16 antibodies analyzed correspond to the theoretical masses expected with effective cleavage of the signal peptide The modification of the signal peptide therefore has no impact on the protein sequence of the antibodies produced.

| Antibody | Fc | | LC | | Fab | |
|---|---|---|---|---|---|---|
| | Theoretical mass (Da) | Experimental mass (Da) | Theoretical mass (Da) | Experimental mass (Da) | Theoretical mass (Da) | Experimental mass (Da) |
| R593 YB2/0 WT (H) | 25 058 | 25 058 | 23 495 | 23 496 | 26 370 | 26 372 |
| R593 YB2/0 AMHRII (E) | 25 058 | 25 058 | 23 495 | 23 497 | 26 370 | 26 372 |
| R593 YB2/0 MB7 (F) | 25 058 | 25 058 | 23 495 | 23 497 | 26 370 | 26 372 |
| R593 YB2/0 XXII49 (G) | 25 058 | 25 058 | 23 495 | 23 496 | 26 370 | 26 372 |
| R593 PER.C6 WT (M) | 25 366 | 25 367 | 23 495 | 23 496 | 26 370 | 26 371 |
| R593 PER.C6 AMHRII (O) | 25 366 | 25 367 | 23 495 | 23 497 | 26 370 | 26 372 |
| R593 PER.C6 MB7 (N) | 25 366 | 25 366 | 23 495 | 23 496 | 26 370 | 26 371 |
| R593 PER.C6 XXII49 (P) | 25 366 | 25 367 | 23 495 | 23 496 | 26 370 | 26 372 |
| R603 YB2/0 WT (D) | 25 058 | 25 058 | 23 168 | 23 170 | 25 197 | 25 200 |
| R603 YB2/0 AMHRII (A) | 25 058 | 25 059 | 23 168 | 23 170 | 25 197 | 25 200 |
| R603 YB2/0 MB7 (B) | 25 058 | 25 059 | 23 168 | 23 170 | 25 197 | 25 200 |
| R603 YB2/0 XXII49 (C) | 25 058 | 25 059 | 23 168 | 23 170 | 25 197 | 25 200 |
| R603 PER.C6 WT (I) | 25 366 | 25 367 | 23 168 | 23 170 | 25 197 | 25 199 |
| R603 PER.C6 AMHRII (K) | 25 366 | 25 367 | 23 168 | 23 169 | 26 197 | 25 199 |
| R603 PER.C6 MB7 (J) | 25 366 | 25 367 | 23 168 | 23 169 | 25 197 | 25 199 |
| R603 PER.C6 XXII49 (L) | 25 366 | 25 367 | 23 168 | 23 169 | 25 197 | 25 199 |

The invention claimed is:

1. A method for producing a recombinant polypeptide of interest in an expression system, comprising introducing a signal peptide into the expression system, said signal peptide comprising at least 12 amino acids and having the sequence of formula (I):

$$(X1)_i X2 X3 X4 S X5 X6 X7 \qquad (I),$$

wherein

X1 is a peptide containing from 3 to 6 amino acids, and i is 0 or 1,

X2 is a peptide containing from 3 to 9 hydrophobic amino acids,

X3 is a peptide containing from 3 to 5 amino acids, said peptide comprising at least 3 contiguous or non-contiguous leucines, X4 is a peptide containing from 2 to 5 amino acids selected from the group consisting of Ala, Thr, Ser, Gln, Ile, and Met, X5 is Ala or Val, X6 is Asn or His, and X7 is Ala or Cys, provided that:

when said signal peptide originates from a natural precursor of a specific protein, said polypeptide of interest is different from said protein, and irrespective of the polypeptide of interest which can be bound to one of said signal peptides in order to be secreted in the extracellular medium.

2. The method according to claim 1, wherein the quantity of the secreted polypeptide corresponds at least to the quantity of said secreted polypeptide using its natural signal peptide.

3. The method according to claim 1, wherein said signal peptide has the sequence of formula (II):

$$M(X1)_i X2 X3 X4 S X5 X6 X7 \qquad (II).$$

4. The method according to claim 3, wherein the peptide X3 comprises at least 3 contiguous leucines.

5. The method according to claim 3, wherein the peptide X3 comprises at least 3 non-contiguous leucines.

6. The method according to claim 3, wherein i=1,

X3 is a peptide constituted by leucines, represented by Ln, wherein n is the number of leucines, n being a number greater than or equal to 3, X4 is a peptide containing from 2 to 5 amino acids selected from the group consisting of Ala, Thr, Ser, Gln, and Ile, X5 is Ala, X6 is Asn, and X7 is Ala, said peptide comprising the following sequence of amino acids:

X1 X2 Ln X4 S A X6 A.

7. The method according to claim 3, wherein
i=1,
X3 is a peptide comprising 3 non-contiguous leucines, and 2 of said leucines are separated by another hydrophobic amino acid selected from the group consisting of Gly, Ala, Val, Ile, Pro, Phe, and Trp,
X4 is a peptide containing from 2 to 5 amino acids selected from the group consisting of Ala, Thr, Ser, Gln, and Ile,
X5 is Val,
X6 is His, and
X7 is Cys,
said peptide comprising the following sequence of amino acids:
X1 X2 X3 X4 S V H C.

8. The method according to claim 1, wherein the expression system is a higher eukaryotic cell line.

9. The method according to claim 8, wherein the higher eukaryotic cell line is selected from the group consisting of SP2/0, SP2/0-Ag 14, NS0, IR983F, Namalwa, Wil-2, Jurkat, Molt-4, PER.C6, HEK293T/17, HEK293, HEK-293.2, Vero, Cos-1, Cos-7, BHK, CHO-K-1, CHO-Lec1, CHO-Lec10, CHO-Lec13, CHO Pro-5, CHO DX B11, CHO DG44, EBx, EB66K6H6, P3X63Ag8.653, YB2/0, CHO-S, and HEK-293F.

10. The method according to claim 1, wherein the expression system is a transgenic animal, selected from the group consisting of goats, sheep, bisons, camels, cows, pigs, rabbits, horses, rats, mice or and llamas.

11. The method according to claim 1, wherein the recombinant polypeptide of interest is selected from the group consisting of a hormone, an enzyme, an immunoglobulin chain, a whole immunoglobulin, or any fragment from an immunoglobulin, a protein involved in the immune response, cytokines, interleukins, complement factors, a chimeric protein, therapeutic proteins, coagulation factors, extracellular matrix proteins, and soluble receptors.

12. The method according to claim 1, wherein the primary and secondary structures of said recombinant polypeptide are identical to those of the secreted polypeptide using its natural signal peptide.

13. A signal peptide comprising at least 12 amino acids and having the sequence of formula III:

$$X1X2X3X4SX5X6X7 \quad (III),$$

wherein
X1 is a peptide containing from 3 to 6 amino acids,
X2 is a peptide containing from 3 to 9 hydrophobic amino acids,
X3 is a peptide containing from 3 to 5 amino acids, said peptide comprising at least 3 contiguous leucines,
X4 is a peptide containing from 2 to 5 amino acids selected from the group consisting of Ala, Thr, Ser, Gln, and Ile,
X5 is Ala,
X6 is Asn, and
X7 is Ala.

14. The signal peptide of claim 13, having the sequence of formula (IV):

$$MX1X2X3X4SX5X6X7 \quad (IV).$$

15. The signal peptide according to claim 13, wherein the signal peptide comprises or consists of the sequence of amino acids: MRWSWIFLLLLSITSANA (SEQ ID NO: 1).

16. An isolated nucleic acid encoding the signal peptide according to claim 13.

17. The nucleic acid according to claim 16, encoding the peptide MRWSWIFLLLLSITSANA (SEQ ID NO: 1).

18. A precursor of a recombinant polypeptide of interest, wherein the precursor has a signal peptide comprising at least 12 amino acids and having the sequence of formula (I):

$$(X1)iX2X3X4SX5X6X7, \quad (I)$$

wherein
X1 is a peptide containing from 3 to 6 amino acids, and i is 0 or 1,
X2 is a peptide containing from 3 to 9 hydrophobic amino acids,
X3 is a peptide containing from 3 to 5 amino acids, said peptide comprising at least 3 contiguous or non-contiguous leucines,
X4 is a peptide containing from 2 to 5 amino acids selected from the group consisting of Ala, Thr, Ser, Gln, Ile, and Met,
X5 is Ala or Val,
X6 is Asn or His, and
X7 is Ala or Cys,
provided that when said signal peptide originates from a natural precursor of a specific protein, said polypeptide of interest is different from said protein, and
irrespective of the polypeptide of interest which can be bound to one of said signal peptides in order to be secreted in the extracellular medium.

19. The precursor of a recombinant polypeptide of interest according to claim 18, wherein the signal peptide has the sequence of formula III:

$$X1X2X3X4SX5X6X7 \quad (III),$$

wherein
X1 is a peptide containing from 3 to 6 amino acids,
X2 is a peptide containing from 3 to 9 hydrophobic amino acids,
X3 is a peptide containing from 3 to 5 amino acids, said peptide comprising at least 3 contiguous leucines,
X4 is a peptide containing from 2 to 5 amino acids selected from the group consisting of Ala, Thr, Ser, Gln, and Ile,
X5 is Ala,
X6 is Asn, and
X7 is Ala.

20. The precursor of a recombinant polypeptide of interest according to claim 18, wherein the signal peptide comprises the following sequence of amino acids:
X1 X2 X3 X4 S V H C,
wherein
X1 is a peptide containing from 3 to 6 amino acids,
X2 is a peptide containing from 3 to 9 hydrophobic amino acids,
X3 is a peptide comprising 3 non-contiguous leucines, wherein 2 of said leucines are separated by another hydrophobic amino acid selected from the group consisting of Gly, Ala, Val, Ile, Pro, Phe, and Trp,
X4 is a peptide containing from 2 to 5 amino acids selected from the group consisting of Ala, Thr, Ser, and Gln,
provided that when said signal peptide originates from a natural precursor of a specific protein, said polypeptide of interest is different from said protein.

21. The precursor of a recombinant polypeptide of interest according to claim 18, wherein said recombinant polypeptide of interest is selected from the group consisting of a hormone, an enzyme, an immunoglobulin chain, a whole immunoglobulin, any fragment derived from an immunoglobulin, a protein involved in the immune response, cytokines, interleukins, complement factors, a chimeric protein, therapeutic proteins, coagulation factors, extracellular matrix proteins, and soluble receptors.

22. An isolated nucleic acid encoding the precursor of a recombinant polypeptide of interest according to claim 18.

23. A vector containing the nucleic acid according to claim 22.

24. A method for producing a recombinant polypeptide of interest, the method comprising:

the addition of a nucleic acid encoding a signal peptide comprising at least 12 amino acids and having the sequence of formula (I):

$$(X1)iX2X3X4SX5X6X7 \qquad (I),$$

wherein

X1 is a peptide containing from 3 to 6 amino acids, and i is 0 or 1,

X2 is a peptide containing from 3 to 9 hydrophobic amino acids,

X3 is a peptide containing from 3 to 5 amino acids, said peptide comprising at least 3 contiguous or non-contiguous leucines, X4 is a peptide containing from 2 to 5 amino acids selected from the group consisting of Ala, Thr, Ser, Gln, Ile, and Met, X5 is Ala or Val, X6 is Asn or His, and X7 is Ala or Cys, to the 5' end of a nucleic acid encoding a recombinant polypeptide of interest, to obtain a nucleic acid encoding the precursor of said recombinant polypeptide of interest, provided that when said signal peptide originates from a natural precursor of a specific protein, said polypeptide of interest is different from said protein, cloning the nucleic acid encoding the precursor obtained in the previous stage into an expression vector, to obtain a vector capable of expressing the precursor of said recombinant polypeptide of interest, transfecting cells of a higher eukaryotic cell line with said vector comprising said nucleotide sequence and expressing said nucleotide sequence, and recovering the recombinant polypeptide of interest secreted in the culture medium.

25. The method according to claim 24, wherein the eukaryotic cell line is selected from the group consisting of SP2/0, SP2/0-Ag 14, NS0, IR983F, Namalwa, Wil-2, Jurkat, Molt-4, PER.C6, HEK293T/17, HEK293, HEK-293.2, Vero, Cos-1 or Cos-7, BHK, CHO-K-1, CHO-Lec1, CHO-Lec10, CHO-Lec13, CHO Pro-5, CHO DX B11, CHO DG44, EBx EB66K6H6, P3X63Ag8.653, YB2/0, CHO-S and HEK-293F.

26. The method according to claim 25, wherein the recombinant polypeptide of interest is selected from the group consisting of a hormone, an enzyme, an immunoglobulin chain, a whole immunoglobulin, any fragment derived from an immunoglobulin, a protein involved in the immune response, cytokines, interleukins, complement factors, a chimeric protein, therapeutic proteins, coagulation factors, extracellular matrix proteins, and soluble receptors.

* * * * *

SEQUENCE LISTING

<160> NUMBER OF SEQ ID NOS: 33

<210> SEQ ID NO 1
<211> LENGTH: 18
<212> TYPE: PRT
<213> ORGANISM: Artificial Sequence
<220> FEATURE:
<223> OTHER INFORMATION: MB7 peptide signal

<400> SEQUENCE: 1

Met Arg Trp Ser Trp Ile Phe Leu Leu Leu Ser Ile Thr Ser Ala
1               5                   10                  15

Asn Ala

<210> SEQ ID NO 2
<211> LENGTH: 19
<212> TYPE: PRT
<213> ORGANISM: Artificial Sequence
<220> FEATURE:
<223> OTHER INFORMATION: 12G4 peptide signal

<400> SEQUENCE: 2

Met Arg Trp Ser Trp Ile Phe Leu Phe Leu Leu Ser Ile Thr Ala Ser
1               5                   10                  15

Val His Cys

<210> SEQ ID NO 3
<211> LENGTH: 19
<212> TYPE: PRT
<213> ORGANISM: Artificial Sequence
<220> FEATURE:
<223> OTHER INFORMATION: XXII49 peptide signal

<400> SEQUENCE: 3

Met Ala Trp Val Trp Thr Leu Leu Phe Leu Met Ala Ala Ala Gln Ser
1               5                   10                  15

Ala Gln Ala

<210> SEQ ID NO 4

```
<211> LENGTH: 54
<212> TYPE: DNA
<213> ORGANISM: Artificial Sequence
<220> FEATURE:
<223> OTHER INFORMATION: MB7 Nucleic acid

<400> SEQUENCE: 4
atgcgatgga gctggatctt cctgctgctg ctgagcatca ccagcgccaa cgcc        54

<210> SEQ ID NO 5
<211> LENGTH: 40
<212> TYPE: DNA
<213> ORGANISM: Artificial Sequence
<220> FEATURE:
<223> OTHER INFORMATION: P1_12G4

<400> SEQUENCE: 5
ctcttgctag cgccgccacc atgcgatgga gctggatctt                        40

<210> SEQ ID NO 6
<211> LENGTH: 40
<212> TYPE: DNA
<213> ORGANISM: Artificial Sequence
<220> FEATURE:
<223> OTHER INFORMATION: P2_12G4

<400> SEQUENCE: 6
cacttgcagt tattgacagg aggaagagaa agatccagct                        40

<210> SEQ ID NO 7
<211> LENGTH: 40
<212> TYPE: DNA
<213> ORGANISM: Artificial Sequence
<220> FEATURE:
<223> OTHER INFORMATION: P3_12G4

<400> SEQUENCE: 7
actgcaagtg tccattgcgc catccggatg acccagtctc                        40

<210> SEQ ID NO 8
<211> LENGTH: 40
<212> TYPE: DNA
<213> ORGANISM: Artificial Sequence
<220> FEATURE:
<223> OTHER INFORMATION: P1_XXII49

<400> SEQUENCE: 8
ctcttgctag cgccgccacc atggcttggg tgtggacctt                        40

<210> SEQ ID NO 9
<211> LENGTH: 40
<212> TYPE: DNA
<213> ORGANISM: Artificial Sequence
<220> FEATURE:
<223> OTHER INFORMATION: P2_XXII49

<400> SEQUENCE: 9
cactttgggc agctgccatc aggaatagca aggtccacac                        40

<210> SEQ ID NO 10
<211> LENGTH: 40
<212> TYPE: DNA
<213> ORGANISM: Artificial Sequence
<220> FEATURE:
<223> OTHER INFORMATION: P3_XXII49

<400> SEQUENCE: 10
```

```
gcccaaagtg cccaagcagc catccggatg acccagtctc                    40
```

<210> SEQ ID NO 11
<211> LENGTH: 40
<212> TYPE: DNA
<213> ORGANISM: Artificial Sequence
<220> FEATURE:
<223> OTHER INFORMATION: P1_D29

<400> SEQUENCE: 11

```
ctcttgctag cgccgccacc atggagcttg ggctgagctg                    40
```

<210> SEQ ID NO 12
<211> LENGTH: 41
<212> TYPE: DNA
<213> ORGANISM: Artificial Sequence
<220> FEATURE:
<223> OTHER INFORMATION: P2_D29

<400> SEQUENCE: 12

```
acacctctta aaagagcaac gagaaaaacc cagctcagcc c                  41
```

<210> SEQ ID NO 13
<211> LENGTH: 40
<212> TYPE: DNA
<213> ORGANISM: Artificial Sequence
<220> FEATURE:
<223> OTHER INFORMATION: P3_D29

<400> SEQUENCE: 13

```
ttaagaggtg tccagtgtgc catccggatg acccagtctc                    40
```

<210> SEQ ID NO 14
<211> LENGTH: 40
<212> TYPE: DNA
<213> ORGANISM: Artificial Sequence
<220> FEATURE:
<223> OTHER INFORMATION: P1_5E5

<400> SEQUENCE: 14

```
ctcttgctag cgccgccacc atgggttgga gctgtatcat                    40
```

<210> SEQ ID NO 15
<211> LENGTH: 42
<212> TYPE: DNA
<213> ORGANISM: Artificial Sequence
<220> FEATURE:
<223> OTHER INFORMATION: P2_5E5

<400> SEQUENCE: 15

```
acacctgtag ctgttgctac cagaaagaag atgatacagc tc                 42
```

<210> SEQ ID NO 16
<211> LENGTH: 41
<212> TYPE: DNA
<213> ORGANISM: Artificial Sequence
<220> FEATURE:
<223> OTHER INFORMATION: P3_5E5

<400> SEQUENCE: 16

```
agctacaggt gtgcactccg ccatccggat gacccagtct c                  41
```

<210> SEQ ID NO 17
<211> LENGTH: 44
<212> TYPE: DNA

```
<213> ORGANISM: Artificial Sequence
<220> FEATURE:
<223> OTHER INFORMATION: P1_CAT13

<400> SEQUENCE: 17
ctcttgctag cgccgccacc atggattttc aagtgcagat tttc                    44

<210> SEQ ID NO 18
<211> LENGTH: 45
<212> TYPE: DNA
<213> ORGANISM: Artificial Sequence
<220> FEATURE:
<223> OTHER INFORMATION: P2_CAT13

<400> SEQUENCE: 18
cattatgact gaagcactga ttagcaggaa gctgaaaatc tgcac                   45

<210> SEQ ID NO 19
<211> LENGTH: 45
<212> TYPE: DNA
<213> ORGANISM: Artificial Sequence
<220> FEATURE:
<223> OTHER INFORMATION: P3_CAT13

<400> SEQUENCE: 19
cttcagtcat aatgtccaga ggagccatcc ggatgaccca gtctc                   45

<210> SEQ ID NO 20
<211> LENGTH: 50
<212> TYPE: DNA
<213> ORGANISM: Artificial Sequence
<220> FEATURE:
<223> OTHER INFORMATION: P1_EPO(H)

<400> SEQUENCE: 20
ctcttgctag cgccgccacc atggggggtgc acgaatgtcc tgcctggctg              50

<210> SEQ ID NO 21
<211> LENGTH: 46
<212> TYPE: DNA
<213> ORGANISM: Artificial Sequence
<220> FEATURE:
<223> OTHER INFORMATION: P2_EPO(H)

<400> SEQUENCE: 21
cagagggagc gacagcaggg acaggagaag ccacagccag gcagga                  46

<210> SEQ ID NO 22
<211> LENGTH: 52
<212> TYPE: DNA
<213> ORGANISM: Artificial Sequence
<220> FEATURE:
<223> OTHER INFORMATION: P3_EPO(H)

<400> SEQUENCE: 22
tcgctccctc tgggcctccc agtcctgggc gccatccgga tgacccagtc tc           52

<210> SEQ ID NO 23
<211> LENGTH: 42
<212> TYPE: DNA
<213> ORGANISM: Artificial Sequence
<220> FEATURE:
<223> OTHER INFORMATION: P1_HAVT20

<400> SEQUENCE: 23
ctcttgctag cgccgccacc atggcatgcc ctggcttcct gt                      42
```

<210> SEQ ID NO 24
<211> LENGTH: 43
<212> TYPE: DNA
<213> ORGANISM: Artificial Sequence
<220> FEATURE:
<223> OTHER INFORMATION: P2_HAVT20

<400> SEQUENCE: 24
aattcaagac aggtggagat cacaagtgcc cacaggaagc cag    43

<210> SEQ ID NO 25
<211> LENGTH: 45
<212> TYPE: DNA
<213> ORGANISM: Artificial Sequence
<220> FEATURE:
<223> OTHER INFORMATION: P3_HAVT20

<400> SEQUENCE: 25
cctgtcttga attttccatg gctgccatcc ggatgaccca gtctc    45

<210> SEQ ID NO 26
<211> LENGTH: 42
<212> TYPE: DNA
<213> ORGANISM: Artificial Sequence
<220> FEATURE:
<223> OTHER INFORMATION: P2_KAPPA_Xba1

<400> SEQUENCE: 26
gcgagctcta gagttcacta acactctccc ctgttgaagc tc    42

<210> SEQ ID NO 27
<211> LENGTH: 20
<212> TYPE: DNA
<213> ORGANISM: Artificial Sequence
<220> FEATURE:
<223> OTHER INFORMATION: 2BGHPA

<400> SEQUENCE: 27
cagatggctg gcaactagaa    20

<210> SEQ ID NO 28
<211> LENGTH: 57
<212> TYPE: DNA
<213> ORGANISM: Artificial Sequence
<220> FEATURE:
<223> OTHER INFORMATION: 12G4 Nucleic acid

<400> SEQUENCE: 28
atgcgatgga gctggatctt tctcttcctc ctgtcaataa ctgcaagtgt ccattgc    57

<210> SEQ ID NO 29
<211> LENGTH: 57
<212> TYPE: DNA
<213> ORGANISM: Artificial Sequence
<220> FEATURE:
<223> OTHER INFORMATION: XXII49 Nucleic acid

<400> SEQUENCE: 29
atggcttggg tgtggacctt gctattcctg atggcagctg cccaaagtgc ccaagca    57

<210> SEQ ID NO 30
<211> LENGTH: 60
<212> TYPE: DNA
<213> ORGANISM: Artificial Sequence
<220> FEATURE:

-continued

```
<223> OTHER INFORMATION: R 593 VL peptide signal

<400> SEQUENCE: 30
atgagggtcc ccgctcagct cctggggctc ctgctgctct ggctcccagg tgccagatgt    60

<210> SEQ ID NO 31
<211> LENGTH: 57
<212> TYPE: DNA
<213> ORGANISM: Artificial Sequence
<220> FEATURE:
<223> OTHER INFORMATION: R 593 VH peptide signal

<400> SEQUENCE: 31
atggagtttg ggctgagctg ggttttcctc gttgctcttt taagaggtgt ccagtgt    57

<210> SEQ ID NO 32
<211> LENGTH: 66
<212> TYPE: DNA
<213> ORGANISM: Artificial Sequence
<220> FEATURE:
<223> OTHER INFORMATION: R603 VL peptide signal

<400> SEQUENCE: 32
atggattttc aagtgcagat tttcagcttc ctgctaatca gtgcttcagt cataatgtcc    60
agagga    66

<210> SEQ ID NO 33
<211> LENGTH: 57
<212> TYPE: DNA
<213> ORGANISM: Artificial Sequence
<220> FEATURE:
<223> OTHER INFORMATION: R603 VH peptide signal

<400> SEQUENCE: 33
atgggattca gcaggatctt tctcttcctc ctgtcagtaa ctacaggtgt ccactcc    57
```